United States Patent
Matsumura et al.

(12)

(10) Patent No.: US 6,251,624 B1
(45) Date of Patent: *Jun. 26, 2001

(54) APPARATUS AND METHOD FOR DETECTING, QUANTIFYING AND CHARACTERIZING MICROORGANISMS

(75) Inventors: Paul M. Matsumura, Cary; Jones M. Hyman, Durham; Scott R. Jeffrey, Raleigh; Martin J. Maresch, Cary; Thurman C. Thorpe, Durham; William G. Barron, Bahama, all of NC (US)

(73) Assignee: Akzo Nobel N.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,678

(22) Filed: Feb. 11, 2000

Related U.S. Application Data

(63) Continuation-in-part of application No. 09/364,903, filed on Jul. 30, 1999, now abandoned, which is a continuation-in-part of application No. 09/267,863, filed on Mar. 12, 1999, now Pat. No. 6,153,400.

(51) Int. Cl.[7] .............. C12Q 1/04; C12Q 1/18; C12Q 1/22; C12Q 1/07
(52) U.S. Cl. .............. 435/34; 435/32; 435/31; 435/29; 435/4
(58) Field of Search .................. 435/34, 32, 31, 435/29, 4, 283.1, 288.3, 288.4

(56) References Cited

U.S. PATENT DOCUMENTS

| Re. 35,286 | 6/1996 | Nelson et al. | 435/39 |
|---|---|---|---|
| 3,272,719 | 9/1966 | Avakian | 435/39 |
| 3,715,280 | 2/1973 | Farmer, III | 435/39 |

(List continued on next page.)

FOREIGN PATENT DOCUMENTS

| 8803814 | 8/1988 | (BR) . |
|---|---|---|
| 1137786 | 10/1979 | (CA) . |
| 2344380 | 5/1982 | (DE) . |
| 3336738 | 8/1983 | (DE) . |
| 102726 | 7/1982 | (EP) . |

(List continued on next page.)

OTHER PUBLICATIONS

Blaser et al, "Antimicrob. Agents Chemother.", V31(17), p1054, Jul. 1987.*

Jenkins et al.; "Rapid Semi Automated Screening and Processing of Urine Specimens"; Clin Microbiol 11 (3) 1980 (abstract only).

(List continued on next page.)

*Primary Examiner*—Louise N. Leary
(74) *Attorney, Agent, or Firm*—Myers Bigel Sibley & Sajovec, P.A.

(57) ABSTRACT

A method and apparatus for performing microbial antibiotic susceptibility testing include disposable, multi-chambered susceptibility plates and an automated plate handler and image acquisition and processing instrument is described. The susceptibility plates are inoculated with a suitable microorganism such as bacteria, fungi, protozoa, algae or viruses and anti-microbial agent(s) are applied that the microorganism is exposed to at a variety of concentrations or a gradient of each anti-microbial agent. The plates are then placed in the instrument, which monitors and measures the growth or lack thereof of the microorganisms. This data is used to determine the susceptibility of the microorganism to the antibiotics. Such a system automates anti-microbial susceptibility testing using solid media and Carbo-Bauer standardized result reporting. The system provides a level of automation previously associated only with broth micro dilution testing, while retaining the advantages of the manual disk diffusion test.

51 Claims, 23 Drawing Sheets

U.S. PATENT DOCUMENTS

| | | |
|---|---|---|
| 3,856,628 | 12/1974 | Sbarra .................................... 435/39 |
| 3,962,040 | 6/1976 | Campbell et al. ...................... 435/39 |
| 4,055,470 | 10/1977 | Sheaff et al. ........................... 435/39 |
| 4,217,411 | 8/1980 | Frock ..................................... 435/39 |
| 4,280,002 | 7/1981 | Bailey et al. ........................... 435/39 |
| 4,468,456 | 8/1984 | Deyloff .................................. 435/39 |
| 4,476,226 | 10/1984 | Hansen et al. ......................... 435/39 |
| 4,565,783 | 1/1986 | Hansen et al. ......................... 435/39 |
| 4,701,850 | 10/1987 | Gibbs ..................................... 435/39 |
| 4,782,014 | 11/1988 | Serban et al. .......................... 435/39 |
| 4,902,630 | 2/1990 | Bennett et al. ........................ 435/39 |
| 5,003,065 | 3/1991 | Merritt et al. ......................... 435/39 |
| 5,089,413 | 2/1992 | Nelson et al. .......................... 435/39 |
| 5,137,812 | 8/1992 | Matner ................................... 435/39 |
| 5,221,628 | 6/1993 | Anderson et al. ..................... 435/39 |
| 5,232,838 | 8/1993 | Nelson et al. .......................... 435/39 |
| 5,290,701 | 3/1994 | Wilkens ................................. 435/39 |
| 5,340,747 | 8/1994 | Eden ...................................... 435/39 |
| 5,344,761 | 9/1994 | Citri ....................................... 435/39 |
| 5,358,852 | 10/1994 | Wu et al. ............................... 435/39 |
| 5,364,766 | 11/1994 | Mach et al. ............................ 435/39 |
| 5,403,722 | 4/1995 | Floeder et al. ......................... 435/39 |
| 5,409,838 | 4/1995 | Wickert ................................. 435/39 |
| 5,443,963 | 8/1995 | Lund et al. ............................. 435/39 |
| 5,462,860 | 10/1995 | Mach ..................................... 435/39 |
| 5,464,755 | 11/1995 | Bochner et al. ....................... 435/39 |
| 5,500,345 | 3/1996 | Soe et al. ............................... 435/39 |
| 5,510,246 | 4/1996 | Morgan ................................. 435/39 |
| 5,541,082 | 7/1996 | Bochner ................................ 435/39 |
| 5,573,950 | 11/1996 | Graessle et al. ....................... 435/39 |
| 5,593,897 | 1/1997 | Potempa et al. ....................... 435/39 |
| 5,627,045 | 5/1997 | Bochner et al. ....................... 435/39 |
| 5,681,712 | 10/1997 | Nelson ................................... 435/39 |

FOREIGN PATENT DOCUMENTS

| | | |
|---|---|---|
| 134976 | 7/1983 | (EP) . |
| 0 576 753 A1 | 7/1992 | (EP) . |
| 751393 | 6/1995 | (EP) . |
| 818680 | 7/1996 | (EP) . |
| 2250439 | 12/1973 | (FR) . |
| 2331992 | 11/1974 | (FR) . |
| 2367825 | 11/1975 | (FR) . |
| 2698702 | 2/1992 | (FR) . |
| 1596154 | 10/1976 | (GB) . |
| 2294319 | 10/1994 | (GB) . |
| 60/083597 | 10/1983 | (JP) . |
| 61/035798 | 7/1984 | (JP) . |
| 61/247377 | 4/1985 | (JP) . |
| 61/260876 | 5/1985 | (JP) . |
| 62-272967 | 5/1986 | (JP) . |
| 2/027259 | 7/1988 | (JP) . |
| 2/055953 | 8/1988 | (JP) . |
| 4/051888 | 6/1990 | (JP) . |
| 4/254760 | 1/1991 | (JP) . |
| 9/121838 | 10/1995 | (JP) . |
| 9/257688 | 3/1996 | (JP) . |
| 2001105 | 10/1987 | (RU) . |
| 1359301 | 12/1987 | (SU) . |
| WO9618720 | 12/1984 | (WO) . |
| WO 8909628 | 4/1988 | (WO) . |
| WO 9100872 | 6/1989 | (WO) . |
| WO9105238 | 9/1989 | (WO) . |
| WO 9105874 | 10/1989 | (WO) . |
| WO 9309438 | 11/1991 | (WO) . |
| WO9318182 | 3/1992 | (WO) . |
| WO 9324530 | 5/1992 | (WO) . |
| WO9500661 | 6/1993 | (WO) . |
| WO9531732 | 5/1994 | (WO) . |
| WO 9606624 | 8/1994 | (WO) . |
| WO 9618721 | 12/1994 | (WO) . |
| WO 9704317 | 7/1995 | (WO) . |
| WO9738128 | 4/1996 | (WO) . |
| WO 98/53301 | 11/1998 | (WO) . |

OTHER PUBLICATIONS

Walsh et al.; "Wstablished Antimicrobial Susceptibility Testing Methods with a New Twist–Points to Consider and a Glimpse of the Future" Adv–Exp–Med–Biol 1994, vol. 349 (abstract only).

Jerris et al.; "An Evaluation of the Video Image Processor in the Aladin for MIC Determinations" Gen Meet AM Soc Microbiol 93 (0) 1993 (abstract only).

Amato et al.; "Novel Application of Video Image Processing to Biochemical and Antimicrobial Susceptibility Testing" Clin–Microbiol 26 (8) 1988 (abstract only).

Navarro et al.; "Comparison of Aladin Video Image Processing to Manual Interpretation of An–Ident." Annu–Meet–AM–Soc–Microbiol 87 (0) 1987 (abstract only).

Malfa et al.; "Critical Evaluatio of the Abbott MS–2 Automatic System in the Rapid Determination of Antibiograms" Quad–Sclavo–Diagn 1985 vol. 21 (1) (abstract only).

Shulman et al.; "Comparison of Aladin Video Image Processing to Manual Interpretation of Uniscept 20E" Annu–Meet–AM–Soc–Microbiol 87 (0) 1987 (abstract only).

Schmitt et al.; "Automated Methods in Microbiological Diagnosis as Compared to Conventional Ones" Zentralbl–Bakteriol–Mikrobiol–Hyg–Ser–A 261 (2) 1986 (abstract only).

Burdash et al.; "Identification of Gram–Negative Bacilli Using the Autobac IDX" Diagn–Microbiol–Infect–Dis 3 (1) 1984 (abstract only).

Jorgensen et al.; "Antibacterial Susceptibility Tests Automated or Instrument–based Methods" Clinical Microbiology 5th edition (abstract only).

Murray et al.; "Overnight Automated Identification Systems" Clinical Microbiology 0 (0) 1987 (abstract only).

McGregor et al.; "The Microscan Walkaway Diagnostic Microbiology System" Pathology 27 (2) 1995 (abstract only).

Perrier–Gros–Claude et al.; "Accuracy for Identification and Antimicrobial Susceptibility of Microscan Fluorogenic Rapid Plates Inoculated From Positive Blood Culture Broth" General meeting of the American Society for Microbiology 95 (0) 1995 (abstract only).

Xander et al.; "Improved Computer–Assisted Reading of Identification and Shortened MIC Data for Reporting on Urine Specimens at a Berlin West Germany University Hospital" Sentralbl–Bakteriol–Mikrobiol–Hyg–Ser 268 (3) 1988 (abstract only).

Buck et al.; "Automated Rapid Identification of Bacteria by Pattern Analysis of Growth Inhibition Progiles Obtained with Autobac 1" Journal Clin–Microbiol 6 (1) 1977 (abstract only).

Fekete et al.; "A Comparison of Serial Plate Agar Dilution, Bauer–Kirby disk Diffusion, and the Vitek AutoMicrobe System for the Determination of Susceptibilities of Klebsiella spp., Enterobacter spp., and *Pseudomonas aeruginosa* to Ten AntiMicrobial Agents" Diagn–Microbiol–Infect–Dis 1994 (abstract only).

Philippin et al.; "Evaluatin of an Automated System in Bacteriology, Application to bacteriological Susceptibility Tests" Pathol–Biol 1991 vol. 39 (5) (abstract only).

Isenberg et al.; "Prototype of a Fully Automated Device for Determination of Bacterial Antibiotic Susceptibility in the Clinical Laboratory" Appl–Microbiol 1971 vol. 22 (6) (abstract only).

Berke et al.; "Comparison of Efficacy and Cost–effectiveness of BIOMIC Video and Vitek Antimicrobial Susceptibilty Test Systems for Use in the Clinical Microbiology Laboratory" J–Clin_Microbiol 1996 vol. 34 (8) (abstract only).

Czeslik et al.; "Chemical Abstracts" Biochemical Methods vol. 124 No. 13 1996 (abstract only).

Azeredo et al.; "Determination of Cell Number and Size of a Population of *Pseudomonas Fluorescens* by Image Analysis" Biotechnology Techniques 11 (5) 1997 (abstract only).

Fruin et al.; "Plate Count Accuracy Analysts and Automatic Colony Counter VS a True Count" J–Food–Prot 40 (8) 1977 (abstract only).

Jeunet et al.; "First Tests with an Artomatic Apparatus for Counting Colonies on Petri Dishes" Revue–Laitiere–Francaise, No. 312, 647, 649, 651, 653, 655 (abstract only).

Patel et al.; "Automated Techniques in Food Microbiology" Food Science +/– Technology Today 3 (2) 1989 (abstract only).

Vasavada et at.; "Evolving Methofologies for Microbiological Examination of Milk and Dairy Foods" Dairy Food and Environmental Sanitation 13 (9) 1993 (abstract only).

Jorgensen et al.; "Automation in Clinical Microbiology" CRC Press 0 (0) 1987 (abstract only).

Woods et al.; "Automation in Clinical Microbiology" AM–J–Clin–Pathol 1992 vol. 98 (abstract only).

Pfaller et al.; "Automated Instrument Approaches to Clinical Microbiology" Diagn–Microbiol–Infect–Dis 1985 vol. 3 (abstract only).

Sharpe et al.; "Mechanizing Microbiology" XIV p. 333 1978 (abstract only).

Treskatis et al.; "Morphological Characterization of Filamentous Microorganisms in Submerged Cultures by on–line Digital Image Analysis and Pattern Recognition" Biotechnology and Bioengineering 53 (2) 1997 (abstract only).

Mc Carty et al., "Historical Perspective on C–Reactive Protein", Laboratory of Bacteriology and Immunology, 1982.

Simmoms et al., "Technical Hematology (third edition)", National Health Laboratories, Plainview, NY.

Husebekk et al., "Scand. J. Immunol." 28 (1988) No. 6,653–658 (abstract only).

Preciado–Patt et al., "Letters in Peptide Science" 5 (1998) No. 5–6,349–355 (abstract only).

Eitoku et al., "Physico Chem. Biol." 37 (193) No. 1,19–23 (abstract only).

McDonald et al., "J. Immunol. Methods" 144 (1991) No. 2,149–155 (abstract only).

Wilkins et al., "Clin. Chem." 40 (1994) No. 7, Part 1, 1284–1290 (abstract only).

Harris et al., "Clin. Res." 37 (1988) No. 2, 614A (abstract only).

Christner et al., "J. Biol. Chem." 269 (1994) No. 13, 9760–9766 (abstract only).

Swanson et al., "Biochim. Biophys. Acta" 1160 (1992) No. 3, 309–316 (abstract only).

Rowe et al., "Clin. Exp. Immunol." 58 (1984) No. 1, 237–244 (abstract only).

Schwalbe et al., Biochemistry: 34 (1995) No. 33, 10432–10439 (abstract only).

Engler, R., C.R. Seances Soc. Biol. Fil. 189 (1995) No. 4, 563–578 (abstract only).

Rybarska et al., J. Physiol. Pharmacol. 46 (1995) No. 2, 221–231 (abstract only).

Maury, C.P.J., "In: Bienvenu, J.J.A., et al. (Eds) Marker Proteins in Inflammation Proceedings", vol. 3, Symposium, Lyon, France, Jun. 26–28, 1985 Berlin, Walter de Gruyter, 1986. p. 153–156 (abstract only).

Spiral Biotech, "Spiral plating specialists—helping microbiologists meet the future since 1976", Product Sheet, 1999.

Jorgensen, J.H., Selection Criteria for the Antimicrobiol Susceptibility Testing System, Jour. Of Clinical Microbiology, Nov. 1993, p. 2841–2844.

Jorgensen, J. et al., Antimicrobial Susceptibility Testing: General Principles and Contemporary Practices, Clinical Infectious Diseases, 1998; 26:973–80.

U.S.Food and Drug Administration Center for Food Safety and Applied Nutrition, "Milk Monitoring with Antimicrobial Drug Screening Tests", Center for Veterinary Medicine Update, Jan. 25, 1996.

Richardson, G.H., Standard Methods for the Examination of Dairy Products, $15^{th}$ Ed. 1985, p.275–279.

Performance Standards for Antimicrobial Disk Susceptibility Tests—Sixth Edition: Approval Standard, National Committee on Clinical Laboratory Standards, vol. 17. No. 1.

Koletar, S.L., *Concepts in Antimicrobial Therapy*, Chapter 3, p.5–96.

"AutoAssay®Systems", product information.

New Test Method Developed for Detecting Drug Residues, USDA ARS Quarterly Report, Jan–Mar 1995.

Jones, G.M. et al., On–Farm Tests for Antibiotic Residues.

"Delvotesto P MINI", product information.

Hill, G.B., *J. Clin. Microbio.* 29 (1991) No. 5, p. 975–979.

Hill, G.B. et al., *Rev. Infect. Dis.*, 12 (1990) Suppl. 2, S200–S209.

Master, P.J., et al., *J. Appl. Bacteriol.*, 51 (1981) No. 2, 253–255.

Schmieger, H., *Prax. Maturwiss.* Biol. 29 (1980) No. 9, 278–280.

Reeves, D.S., et al., *Anitmicrob. Agents Chemother.*, 18 (1980) No. 6, 844–852.

Dougherty, P.F. et al., *Antimicrob,. Agents Chemother.* 11 (1977) No. 2, 225–258.

Joly–Guillou, M.L. et al., *Pathol. Biol.*, 35 (1987) No. 5, 563–567.

Le Noc, P., et al., *Pathol. Biol.*, 33 (1985) No. 9, 906–910.

Boucaud–Maitre, Y., et al., *Pathol. Biol.*, 44 (1996) No. 5, 363–366.

Christensen, JJ, et al. *J. Antimicrobial Chemother.*, 38, (1996) No. 2, 253–258.

Chang, J.C., et al., *Antimicrob. Agents Chemother.*, 41 (1997) No. 6, 1301–1306.

Marco, F., et al., *Diagnost. Microbiol. Infect. Dis.*, 29 (1997) No. 1, 55–57.

Dyck, E. van, et al., *J. Clinical Microbiol.*, 32 (1994) No. 6, 1586–1588.

Shapiro, M.A. et al., *J. Clinical Microbiol.*, 20, (1984) No. 4, 828–830.

Chernomordick, AB et al., *Antibiotiki*, 25 (1980) No. 11, 834–337.

LiMuti et al., *Journal of Microbiological Methods*, 9:129–137, 1989.

Y. Umemoto, *Agr. Biol. Chem.*, 33:11:1651–1653, 1969.

Y. Yamazaki et al., *Z. Naturforsch*, 42c:1082–1088, 1987.

Y. Umemoto et al., *Milchwissenschaft,* 30(10):591–594, 1975.

N. Balayev et al., *J. of Biochem. and Biophys. Methods,* 25:125–132, 1992.

P. Jones et al., *Nucleic Acids Research,* 20:17:4599–4606, 1992.

A. Gavoille et al., *Comput. Biol. Med.,* 24:3:179–188, 1994.

A. Singh et al., *Applied and Environmental Microbiology ,* 56:2:389–394, 1990.

S. Hammonds et al., *Letters in Applied Microbiology,* 10:27–29, 1990.

S. Eins, *Microscope,* 22:59–68, 1974.

M. Calicchia et al., *Journal of Food Protection,* 57:10:859–864, 1994.

M. Fernandes et al., *CABIOS,* 4:2:291–295, 1988.

J. Leyden et al., *Journal of Hospital Infection,* 18B:13–22, 1991.

R. Mueller et al., *Biotechnology and Bioengineering,* 39:11:1161–1170, 1992.

M. Smith et al., *In Vitro Cellular and Decelopmental Biology,* 23:1:67–74, 1987.

"3M Pertifilm Test Kit—HEV" Product Information Sheet.

"Petrifilm™ Test Kit—HEC" Product Insert.

3M, "Lift your lab to a new level of efficiency", Product Sheet.

3M "Pertifilm™ Enterobacteriaceae Count Plates" Product Sheet, 1991.

* cited by examiner

APPARATUS AND METHOD FOR DETECTING, QUANTIFYING AND CHARACTERIZING MICROORGANISMS

RELATED APPLICATIONS

This application is a continuation-in-part of U.S. application Ser. No. 09/364,903, filed Jul. 30, 1999 (now abandoned), which is a continuation-in-part of U.S. application Ser. No. 09/267,863, filed Mar. 12, 1999 (now U.S. Pat. No. 6,153,400).

This application is related to U.S. patent application Ser. No. 08/989,560 to Jeffrey et al. filed Dec. 12, 1997, and U.S. patent application Ser. No. 09/267,863 to Matsumura et al., filed Mar. 12, 1999, the subject matter of each being incorporated herein by reference.

BACKGROUND OF THE INVENTION

The presence of microbial contamination in clinical specimens is conventionally determined by culturing the specimens in the presence of nutrients and detecting microbial activity through changes in the specimen or in the atmosphere over the specimen after a period of time. For example, in the U.S. Pat. No. 4,182,656 to Ahnell et al., the sample is placed in a container with a culture medium comprising a carbon 13 labeled fermentable substrate. After sealing the container and subjecting the specimen to conditions conducive to biological activity, the ratio of carbon 13 to carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the pressure of gas in the container. U.S. Pat. No. 4,073,691 provides a method for determining the presence of biologically active agents, including bacteria, in a sealed container containing a culture medium by measuring changes in the character if the gaseous atmosphere over the specimen after a period of time.

A method for non-invasive detection is taught by Calandra et al., U.S. Pat. No. 5,094,955, where a device is disclosed for detecting the presence of microorganisms in clinical specimens, such as blood or other body fluids, and in non-clinical specimens, by culturing the specimens with a sterile liquid growth medium in a transparent sealed container. The presence of microorganisms is determined by detecting or measuring changes in the pH of the specimen or the production of carbon dioxide within the specimen using a sensor affixed to the interior surface of the container or to the sealing means used to seal the container. In Calandra et al., microorganisms can be detected in the presence of interfering material, such as large concentrations of red blood cells, through non-radiometric and non-invasive means.

One disadvantage of the detection system of Calandra et al., is that the time required for detecting the presence of microorganisms is related to the number of microorganisms within the sample. Also, because the growth medium for the microorganisms is a liquid, the container must usually be agitated during incubation, which is an additional expense involved in making the incubation equipment, as well as an increase in the likelihood of a mechanical breakdown. Also, such a system allows for the determination of the presence of microorganisms, but does not allow for enumeration. Furthermore, it is often the case that after detection of microorganisms, it is desired to identify the microorganisms and/or determine their susceptibility to various antibiotics. In a Calandra-type system, it would be necessary to plate out the microorganisms from the liquid culture medium before performing susceptibility or identification tests, which involves additional time—time that is not always available if the patient is very ill. Also, a Calandra-type system could not serve the additional functions of reading/imaging plates for antibiotic susceptibility and/or microbial identification.

Following detection of a microorganism in a patient sample, it is often desirable to determine to which antibiotics the microorganism is susceptible. There are now a number of bacterial species which increasingly exhibit resistance to one or more classes of antimicrobial agents, making it that much more important to perform susceptibility testing. Failure of a particular susceptibility test to accurately predict antimicrobial resistance in a patient's isolate could significantly impact patient care if an antibiotic is used to which the microorganism is not susceptible.

Different types of susceptibility tests can be used to test a microorganism. The following brief descriptions give details of some known susceptibility tests as well as some details that relate to the present invention.

One type of susceptibility test is the disk diffusion test, often referred to as the Kirby-Bauer test. This is a standardized test that involves inoculating (with 0.5 McFarland standardized suspension of a microbial isolate) a gel plate (e.g. a 150-mm Mueller-Hinton agar plate) and placing thereon one or more disks impregnated with fixed concentrations of antibiotics. After incubation (e.g. 18–24 hours at 35 degrees C.), the diameter of zones of inhibition around the disks (if present) determine the sensitivity of the inoculated microorganism to the particular antimicrobial agent impregnated in each disk. Due to the standardization of the Kirby-Bauer method, results of this method are analyzed by comparing the diameter of the inhibition zone with information published by NCCLS (National Committee on Clinical Laboratory Standards) in *Performance Standards for Antimicrobial Disk Susceptibility Testing*, the subject matter of which is incorporated herein by reference. The results of this test are semi-quantitative in that there are three categories of susceptibility—namely resistant, intermediate and susceptible. As can be seen in FIG. 14, an agar plate 110 with inoculum has a plurality of disks 112 placed thereon, which disks are impregnated with antibiotics (of different types and/or concentrations). After incubation, zones of microbial growth inhibition 114 are formed. These zones 114 are interpreted to indicate resistant, intermediate or susceptible microorganisms based on NCCLS criteria.

Another method of antimicrobial susceptibility testing is the antibiotic gradient method. This test utilizes an antibiotic gradient in a gel medium. Paper or plastic strips are impregnated with an antibiotic concentration gradient. A plurality of strips is placed on a Mueller-Hinton agar plate like spokes on a wheel, with the plate having been inoculated with the microorganism to be tested. After incubation, an antibiotic gradient is formed in the gel in an elliptical shape around each test strip (if the microorganism is susceptible to the antibiotic on the particular strip). The minimum concentration of the antimicrobial agent that prevents visible microorganism growth is the endpoint of the test (the minimum inhibitory concentration, or MIC). Put in other words, in disk diffusion testing, the MIC is the concentration at the edge of the inhibition zone (the growth/no growth boundary). In this case, the MIC is the point at which the elliptical growth inhibition area intersects the test strip. As can be seen in FIG. 15, agar plate 101 has a plurality of test strips 103 that are impregnated with an antibiotic gradient.

Elliptical zones 105 are formed where microorganism growth is inhibited by the antibiotic agent in/on the test strip. Point 107 where the elliptical zone intersects the test strip is the MIC point.

A third type of susceptibility test is the broth dilution test. In this type of test, dilutions of antibiotics (e.g. consecutive two-fold dilutions) are prepared. Often, at least ten concentrations of a drug are prepared in tubes or microwells. Each tube or well having the various concentrations of antibiotics is inoculated with a particular microorganism (a standardized suspension of test bacteria is added to each dilution to obtain a final concentration of $5 \times 10^5$ CFU/ml). A growth control well and an uninoculated control well are included on each plate. After incubation (e.g. for 16–24 hours at 35 degrees C.), the wells or tubes are examined manually or by machine for turbidity, haze and/or pellet. Indicators can be placed in the wells to facilitate the visualization of microbial growth. As with other tests, the minimum concentration of antimicrobial agent that prevents visible microbial growth is the MIC.

Commercial microdilution tests are typically performed on standard 96 well plates, each well holding approximately 100 to 200 microliters with commercially prepared antibiotic test panels. With 96 wells and 2 to 10 different dilutions for each antibiotic, numerous antibiotics can be tested on a single plate. A significant problem with such commercial microdilution systems is the inflexibility of the standard antibiotic test panels. The commercial plates are manufactured with various amounts of frozen, dried or lyophilized antimicrobial agents in the wells. This avoids the time consuming task of preparing the plates. However, due to the availability of many antibiotics (more than fifty in the United States), it is often problematic for a laboratory to find a standard commercial test panel which is ideal for that laboratory's needs. FIG. 16 is an illustration of a 96-well plate used in such a microdilution system.

A variation of the broth microdilution method is set forth in U.S. Pat. No. 5,501,959. This system uses microtiter plates with 168 wells, each containing a paper disk attached to the bottom of the well. The disks contain serial two-fold dilution concentrations of various antimicrobial agents, as well as a redox indicator. Up to 20 different antimicrobial agents can be tested on a plate. This use of paper disks simplifies the manufacture of the custom panels. However, higher costs are involved when a susceptibility test is custom made for a customer.

Current instruments that offer the highest degree of automation in susceptibility testing are typically based on automating the tasks performed in the manual broth microdilution method mentioned above. One such example is the instrument described in U.S. Pat. No. 4,448,534. This instrument uses multi-well plates that are pre-loaded with serial two-fold dilution concentrations of antimicrobial agents. Plates are inoculated manually and placed in the instrument, where they are incubated. At the appropriate times, the wells on the plate are read by a photometer/fluorometer to determine the results of the test. Another automated system is described in U.S. Pat. No. 3,957,583. This instrument uses small multi-chamber cards that are pre-loaded with serial two-fold dilution concentrations of antimicrobial agents. Cards are inoculated automatically, incubated, and monitored within the instrument. This instrument reads the chambers in the card periodically using a photometer. These kinetic measurements yield growth curves that allow the instrument to determine the results of the test. Though the aforementioned instruments perform testing in 4 to 8 hours, they may fail to detect induced resistance of the microorganism, which could result in an incorrect susceptibility report Unfortunately, the degree of automation that is provided by instruments based on broth microdilution is not available for methods such as disk diffusion.

Regarding microbial identification, various selective and differential media have been relied upon for determining which type of microorganism has been detected. Selective media are appropriate when testing for specific genera or species of microorganisms and act by inhibiting all (or nearly all) microorganisms except the target microorganism. Differential media are used to distinguish between certain species of bacteria based on a particular trait (e.g. the ability to metabolize citrate as a sole carbon/energy source). In a hospital or environmental setting, the different species one might encounter are of such an overwhelming number, that the use of selective media is prohibitive. Microbial identification in these settings is then based on metabolic characteristics. Conventional techniques require a large time commitment for the preparation of the appropriate media and much laboratory space using traditional equipment.

There are also a variety of automated instruments that exist for identification of microorganisms. In one such instrument, small multi-chambered cards contain a variety of substrates. The chambers are measured photometrically. Based on the pattern of substrates metabolized, identification is determined. Another system uses a 96 well plate. Each well contains an individual carbon source and red-ox indicator. Identification is determined based on the pattern of substrate utilization. Still another system uses fluorescent dyes and substrates labeled with fluorescent compounds. Enzymatic activity releases the fluorescent compound from these substrates or changes in the pH result in a change in the intensity of the fluorescence.

SUMMARY OF THE INVENTION

The present invention relates to detection and/or screening of microorganisms on an instrument, and concurrently or consecutively on the same instrument, determining the susceptibility of microorganisms to various antibiotics and/or identifying microorganisms. The invention also relates to optionally performing urine screening within the same instrument. The instrument employs image acquisition technology, several image processing algorithms, and a variety of specialized disposable plates to perform these functions.

More particularly, the instrument employs disposable plates for culturing microbial organisms, and computer hardware and software to facilitate detection and/or measurement by the instrument. Because the system performs a variety of functions, there are several types of specialized plates that are used within the instrument. Each type of plate is optimally configured for its particular function; hence, the plates may differ significantly in terms of culturing and detection properties, and physical dimensions. However, all plates, regardless of type, can be processed by the instrument The instrument is capable of performing multiple measurements on each plate over time and utilizing this kinetic rate information to more accurately perform each function.

BRIEF DESCRIPTION OF THE DRAWINGS

FIG. 18a illustrates elongated channels with antibiotic disks, and where FIG. 18b illustrates shorter channels, some with antibiotic disks therein;

FIG. 19a illustrates an embodiment with elongated channels each having an antibiotic strip therein, whereas

FIG. 20a shows a raw image and FIG. 20b shows a processed image;

FIG. 21a shows a raw image and FIG. 21b shows a processed image;

FIG. 22a is an unprocessed image after 4 hours, FIG. 22b is a processed image after 4 hours, FIG. 22c is an unprocessed image after 18 hours, and FIG. 22d is a processed image after 18 hours;

FIG. 23a is a plate viewed at a wavelength of visible light after 24 hours, and FIG. 23b is a plate viewed in the ultraviolet range;

DETAILED DESCRIPTION OF THE PREFERRED EMBODIMENT

Figure 1:
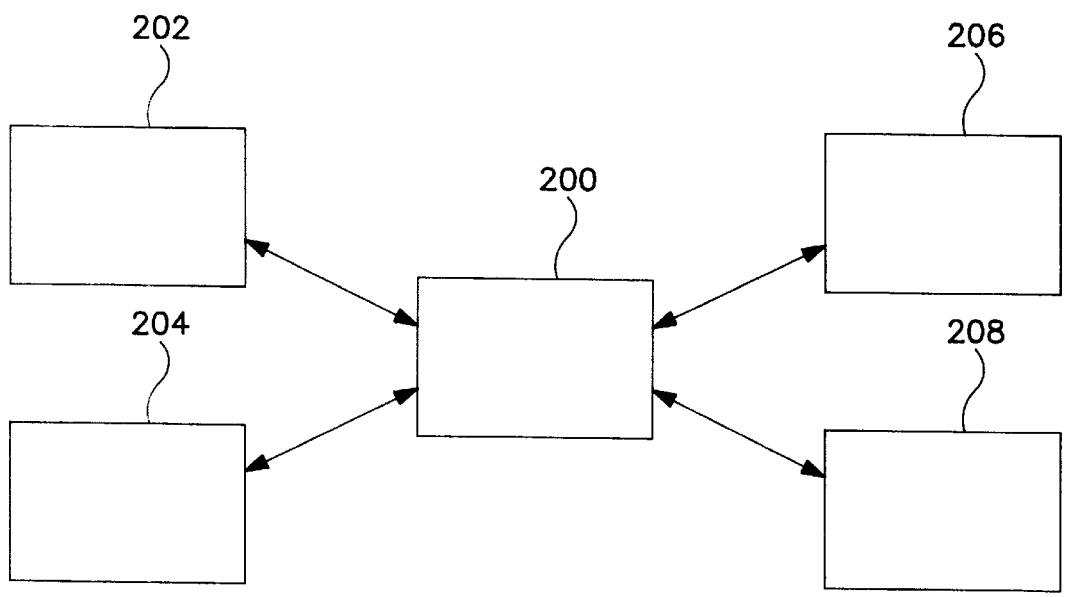
FIG. 1 is a block diagram of the main components of the multi-functional instrument.

As can be seen in FIG. 1, a processing subsystem 200 is provided in communication with a user interface subsystem 202, a plate transport subsystem 204, incubation subsystem 206 and imaging subsystem 208. The processing subsystem is responsible for controlling the operation of the instrument, and is based on an embedded microprocessor (e.g., Pentium™) or microcontroller board or system, such as a PC. Using various parallel or serial interfaces, the processing subsystem communicates with, as well as controls, the other subsystems. The processing subsystem also provides the capability to perform analysis of acquired data. The user interface subsystem provides the capability for users to control the instrument, as well as view control parameters and/or data from the instrument. The user interface subsystem is comprised of a CRT, LCD, CCD, and/or CMOS display, coupled with discrete buttons, a barcode reader, a keypad, a keyboard, and/or a touchscreen. Audio input (with speech recognition) and output capabilities may also be provided. The incubation subsystem provides the capability for regulating temperature and/or humidity within the incubation chamber of the instrument, while the plate transport subsystem provides the capability to control the movement of devices within the instrument. The imaging subsystem provides the capability to acquire images of the plates, and comprises various image capture and illumination devices.

Generally, the instrument is responsible for performing three main functions (though additional functions are envisioned): plate incubation, image acquisition, and image processing. The instrument provides a controlled environment to incubate the various plates for optimal growth conditions. The plates (detection/enumeration sensor plates, antibiotic susceptibility plates, identification plates, urine screening plates, etc.) are inoculated and placed in the incubator where they are subsequently scanned at regular intervals by an image acquisition device during the incubation period. The instrument provides for image acquisition using one or more color and/or gray scale imaging and illumination devices. The time-lapsed images are obtained from one or more sides (views and angles) of the plates. Images acquired during the incubation period are analyzed using several image processing techniques and algorithms to determine results. The instrument design can be modular such that it can be configured to provide a wide range of plate incubation capacity.

Figure 2:
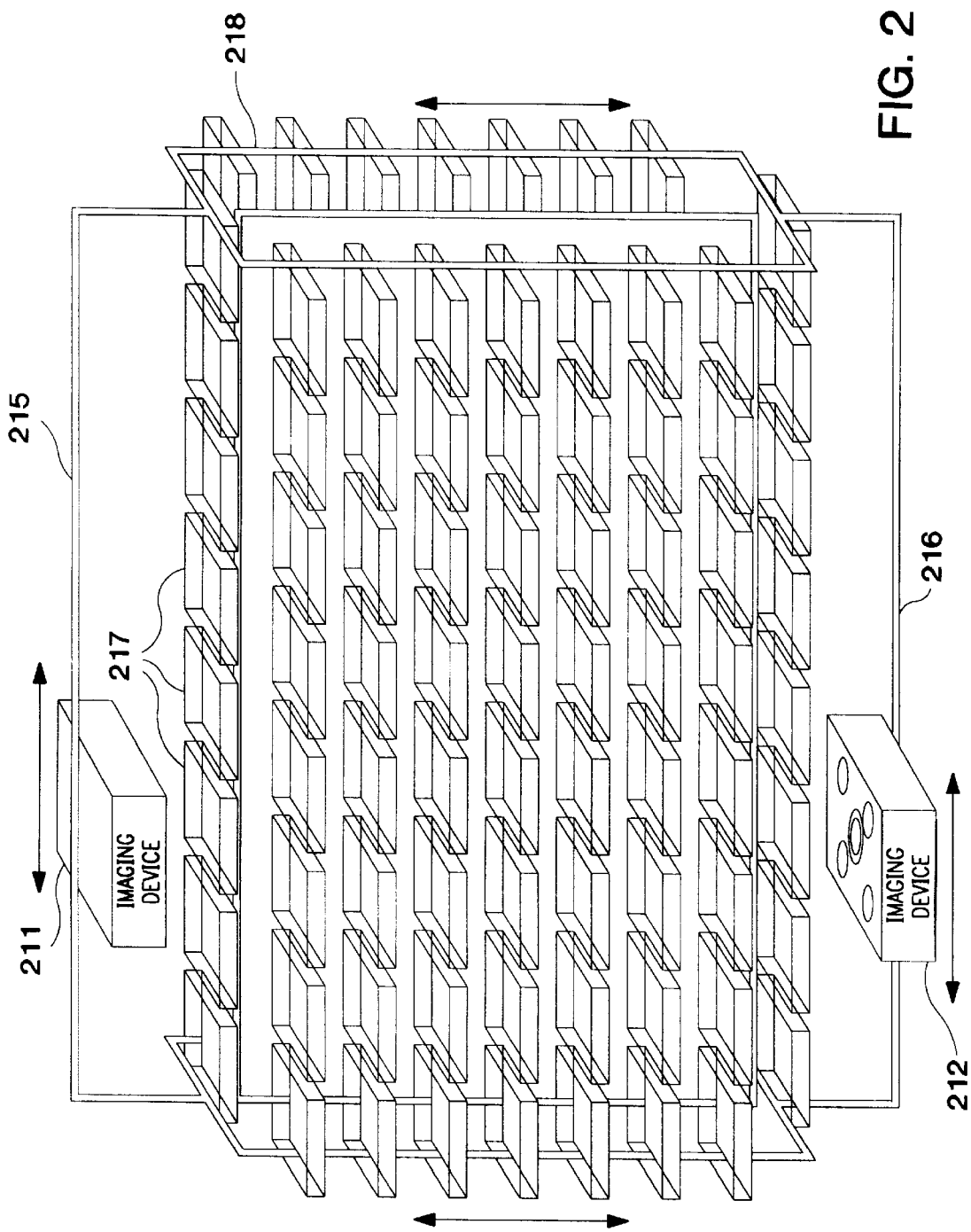
FIG. 2 is an illustration of one embodiment of the invention showing different types of plates, imaging devices, and transport systems.

One example of how the variety of plates could be moved relative to one or more imaging devices is illustrated in FIG. 2. As can be seen in this figure, imaging devices 211 and 212 are provided for capturing the image of the top and bottom, respectively, of each plate. Top and bottom imaging transport systems 215 and 216 are provided for moving the respective imaging devices past a plurality of plates when the plates are disposed at the top or bottom imaging station. Each plate 217 at each imaging station has its image captured by an imaging device. Plates are moved to the imaging stations by a plate transport system 218 that, as in FIG. 2, moves plates both upwardly and downwardly from the imaging stations. In one possible configuration, plate shelves holding the plates are transported down the front side of the instrument and up the rear side. The imaging devices are mounted on linear tracks at the top and bottom positions of the rotating track. The plate shelves are rotated "stepwise" within the instrument. The plate shelves at the top and bottom positions of the rotating track enter "imaging stations". The imaging devices are tracked along the length of the shelves, capturing image data. Plate shelves are then rotated another "step", and other shelves are moved into the imaging locations for image capture. Though the different types of plates are illustrated as being the same size, the plate holders can also be constructed to hold plates of varying sizes, or different plate holders could each hold plates of a particular size, with plate sizes varying between plate holders.

Figure 3:
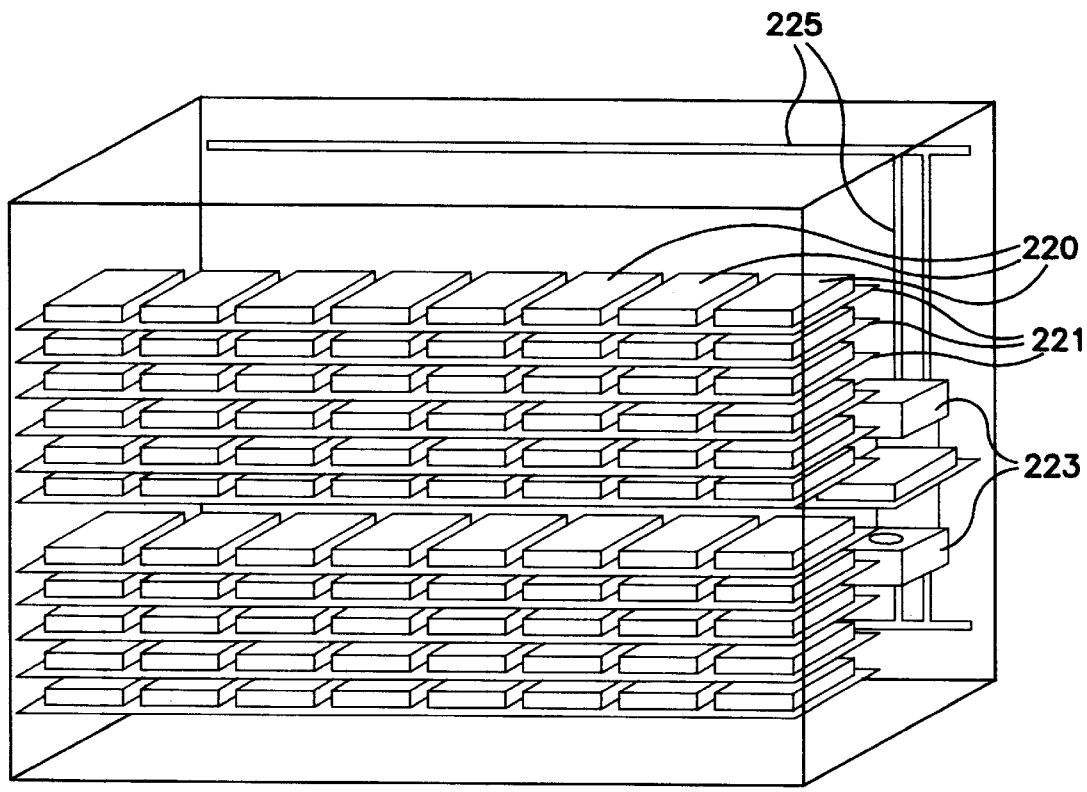
FIG. 3 is an illustration of another embodiment of the invention showing plates, plate shelves, imaging/lighting devices and transport mechanisms.
Figure 4:
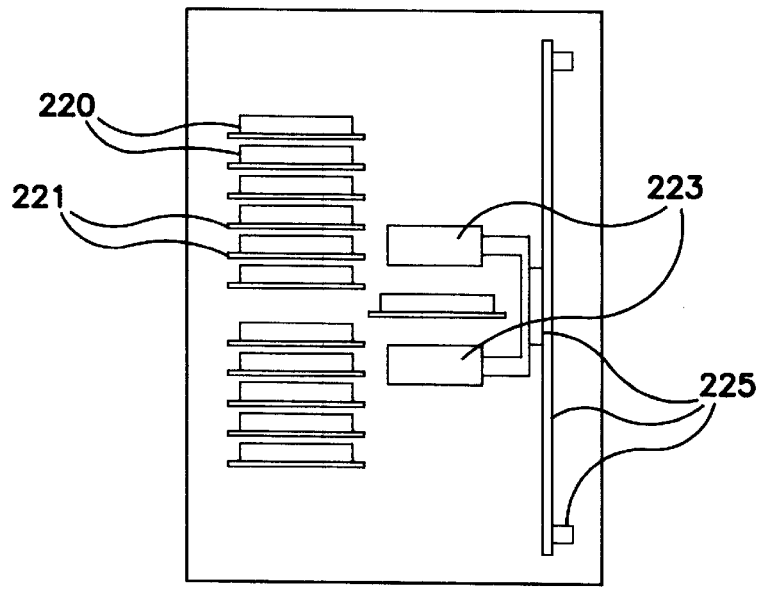
FIG. 4 is an illustration of a cross section of the embodiment shown in FIG. 3.

In another embodiment of the invention, as can be seen FIGS. 3 and 4, a plurality of plates 220 are held on plate shelves 221. The plate shelves are "stacked" only on the front side of the instrument. Shelves are mounted on slide bearings that allow them to slide back into the instrument for imaging. The imaging/lighting devices 223 are mounted on an imaging/lighting transport mechanism 225, such as an X-Y tracking mechanism behind the shelves. Plates are imaged in the following manner:

a) The imaging devices are moved into position (aligned with the level of the shelf) behind the shelf;
b) The shelf is pulled back into the instrument along linear bearings, between imaging devices;
c) The imaging devices are tracked along the length of the shelf, capturing image data;
d) The shelf is pushed forward, and the imaging devices are moved to image the next shelf.

Figure 5:
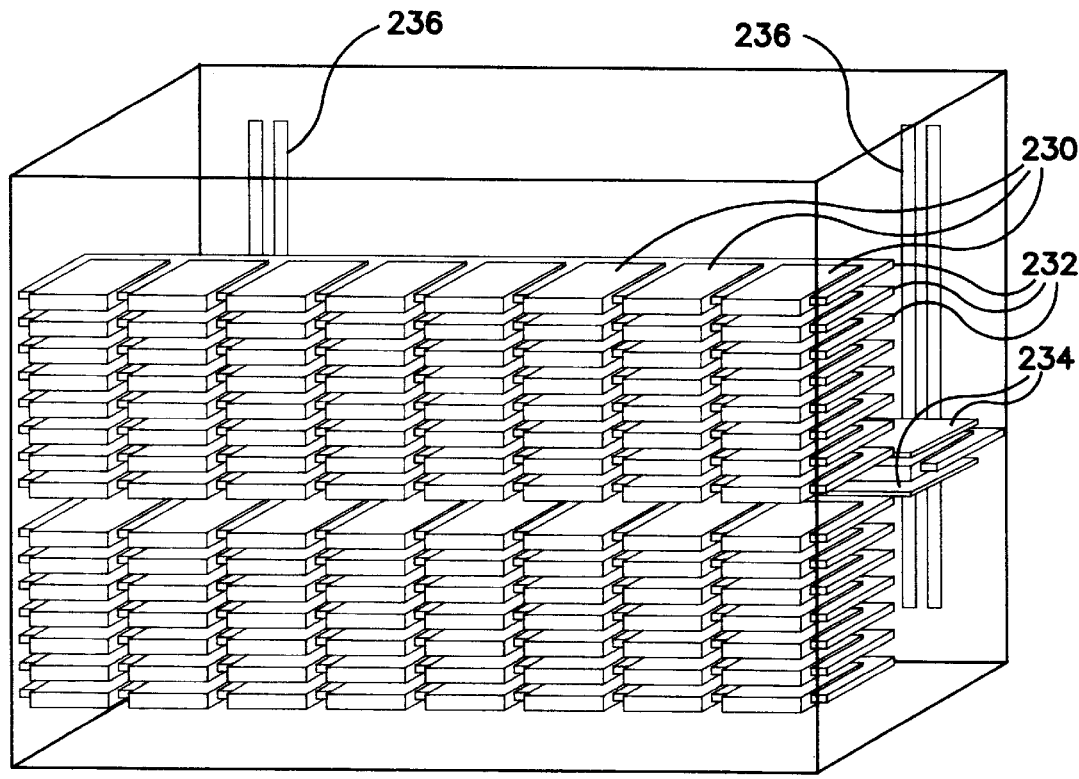
FIG. 5 is an illustration of an additional embodiment of the instrument of the invention.
Figure 6:
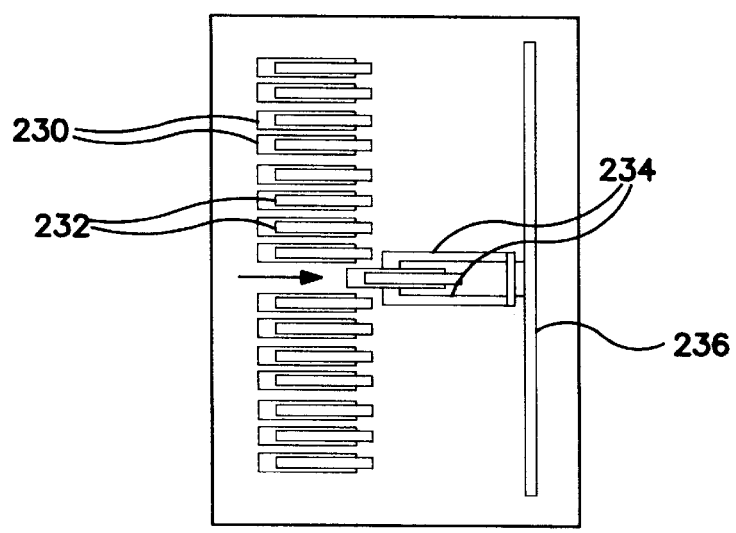
FIG. 6 is an illustration of a cross section of the embodiment illustrated in FIG. 5.

In a further embodiment of the invention as can be seen in FIGS. 5 and 6, plates 230 are held on plate shelves 232 (the plate shelves can be configured in the same manner as in FIGS. 3 and 4). The imaging devices 234, are provided as long scanner arrays arranged along the length of the shelves. Plates are imaged in the following manner:

a) The scanner arrays are moved into position by a scanner transport mechanism 236 (aligned with the level of the shelf) behind the shelf;
b) The shelf is pulled back into the instrument along linear bearings, between the scanner arrays;
c) As the shelf is pulled back, all of the plates on this shelf are imaged simultaneously by the array of scanners; and
d) The shelf is pushed forward, and the scanner arrays are moved to image the next shelf.

Figure 7:
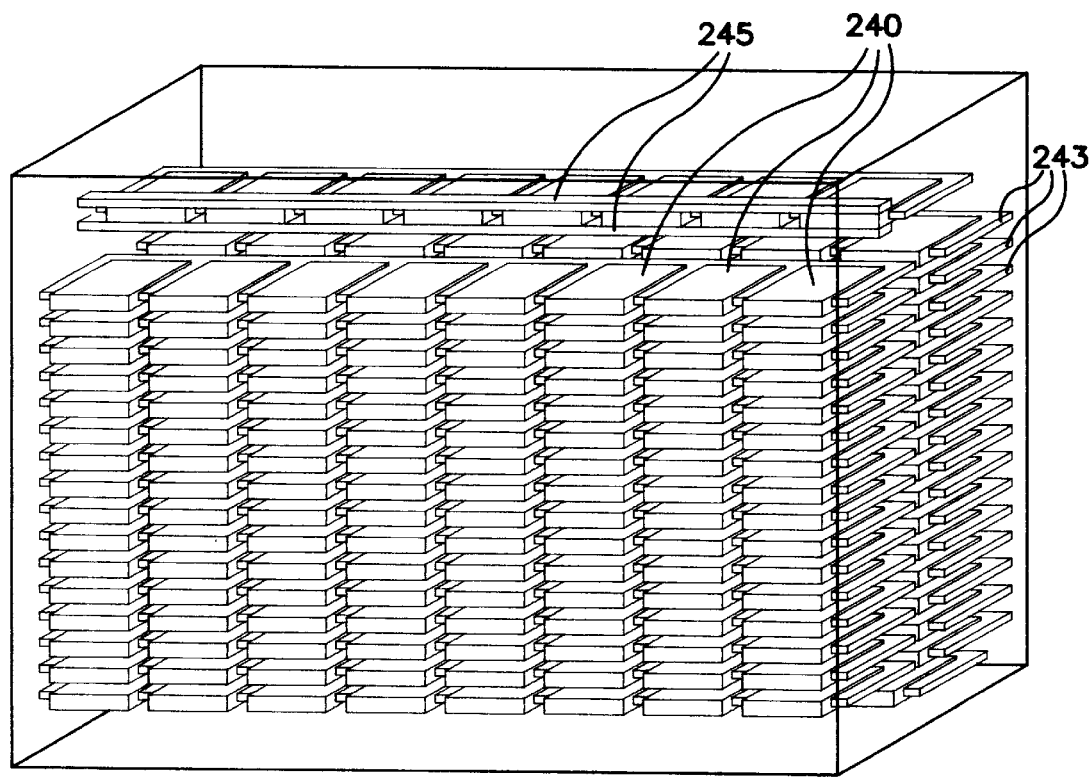
FIG. 7 is an illustration of yet another embodiment of the instrument of the invention.
Figure 8:
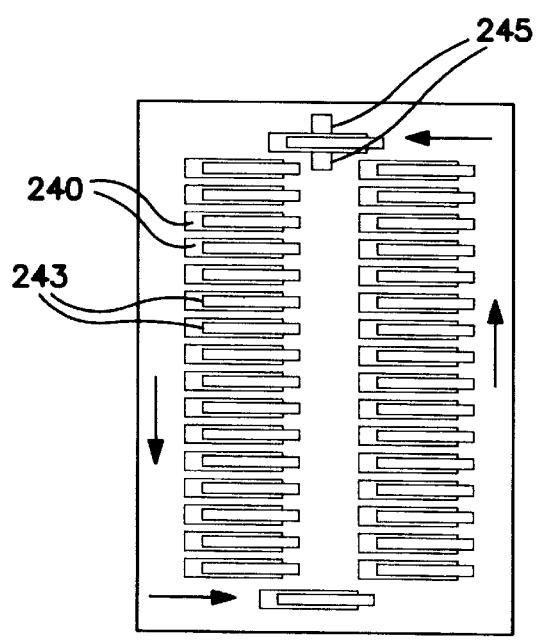
FIG. 8 is an illustration of a cross section of the embodiment illustrated in FIG. 7.

In yet another embodiment of the invention, as illustrated in FIGS. 7 and 8, plate shelves 243 with plates 240 thereon are moved within the instrument on a rotating track (as in FIG. 2). As in FIG. 5, the imaging devices 245 are scanner arrays arranged along the length of the shelves—however these arrays are fixed at the top of the instrument. Plates 240 are imaged in the following manner:

a) Plate shelves are rotated "stepwise" within the instrument;
b) As the shelves are moved from the back of the instrument towards the front (at the top of the rotating rack), they pass between the scanner arrays (mounted at the top of the instrument) where all plates are imaged simultaneously; and
c) Plate shelves are rotated another "step", and another shelf is moved through the scanner arrays for image capture.

Of course other plate and/or imaging device transport systems could be utilized. A cartridge system could be used, where one plate at a time is removed from a stack for imaging (and either the stack or imaging device is moved to position the imaging device and selected plate in proximity to each other). A turntable or other rotary system could be used to position each plate proximate to an imaging device, or a conveyor belt or wheel system could be used, where plates (with solid media) are affixed to a belt or wheel in rows and are turned upside down depending upon which side of the belt or wheel the plate is on.

The instrument provides for image acquisition using one or more color and/or gray scale imaging devices: CCD linear array scanner, a CCD line-scan camera, a CCD 2D array camera (still or motion video), a laser scanning camera, or other device that would provide a sufficiently clear image of the plate that can be used alone or after further processing. By "image" it is meant any information, such as optical information, from the plate that is $\geq$ a 1×1 pixel. The image acquisition is performed at regular pre-programmed intervals, with the captured image obtained from one or more views and angles of the plate.

Images acquired during the incubation period are analyzed using one or more image processing techniques. In the example of FIG. 2, images are acquired from both the top and bottom of the plate at regular intervals (though imaging only one side of the plate is also envisioned). Typically the interval is from 5 minutes to 4 hours, though preferably the interval is between one half-hour and 2 hours, and most preferably every hour. Scanning at regular intervals provides kinetic growth data, which may be used to help characterize the microorganisms. The image-processing algorithm implemented to determine results on each plate is comprised of one or more of the following steps:

a) Color Separation and Selection (if required)—to select the color band of interest (sensor dependent);
b) Image Masking—to isolate the area of interest from extraneous image data;
c) Image Subtraction—to isolate the areas of change between two images taken at subsequent time intervals;
d) Image Equalization—to amplify the magnitude of the changes appearing in the subtracted image;
e) Image Blurring—to reduce the effects of single pixel noise in the equalized image (e.g. low pass filter);
f) Image Contrast and Brightness Enhancement—to further amplify localized differences in the filtered image;
g) Image Thresholding (with several thresholds, if required)—to prepare the image for the colony detection/enumeration algorithm;
h) Processed Image Analysis using one of the following (or other) functions depending on the plate being analyzed—
  1) Colony Detection, Enumeration and/or Classification—to determine the presence of microbial organisms on the plate, to enumerate the number of colonies on the plate, and/or to perform color analysis to classify colonies on the plate; or
  2) Inhibition Zone Detection and Measurement—to determine the susceptibility of microbial organisms to a particular antibiotic; or
  3) Substrate Reaction Zone Inspection—to determine the extent of substrate reaction by color analysis.

Plates can be illuminated by a separate lighting mechanism, or the light source can be provided as an integral part of the imaging device. The light source can be broadband and/or narrowband visible, ultraviolet and/or infrared illumination.

Figure 9:
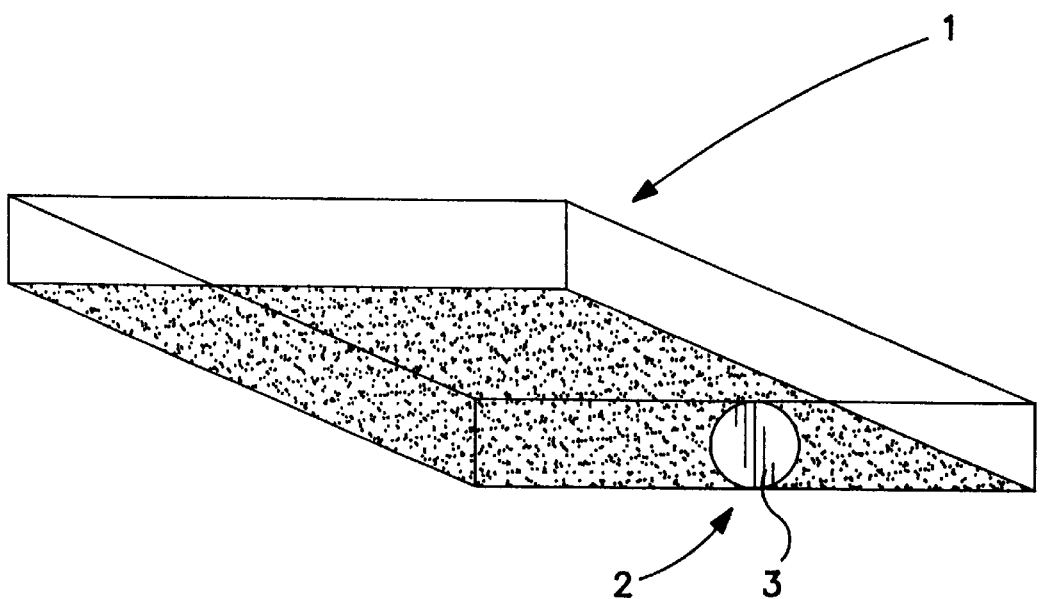
FIG. 9 is an illustration of a microbial detection (sensor) plate.

As will be explained below, a variety of plates can be handled and analyzed, all within the same instrument:

Detection/Enumeration Plate:

FIG. 9 is an illustration of sensor plate 1 that can be in the form of a flat, shallow container with at least one side (e.g. the bottom side) being transparent or translucent Though the container can be open (or even simply a substrate), it is preferably a sealed or sealable container, and preferably with an amount of headspace above the sensor plate layers. The container can be provided with a port 2, which may be sealed with a stopper 3, screw-cap, septum, or any combination thereof (or any other sealing device). Once a sample is collected into the container, the sensor plate can be configured as either a gas-permeable or a gas-impermeable container, depending on the growth requirements of the microorganism. This configuration is accomplished by using different plate composition materials, laminates (gas impermeable and/or hydrophobic gas-permeable membranes), and/or configurable vents (eg. a gas permeable membrane in an opening of the container wall).

Figure 10:
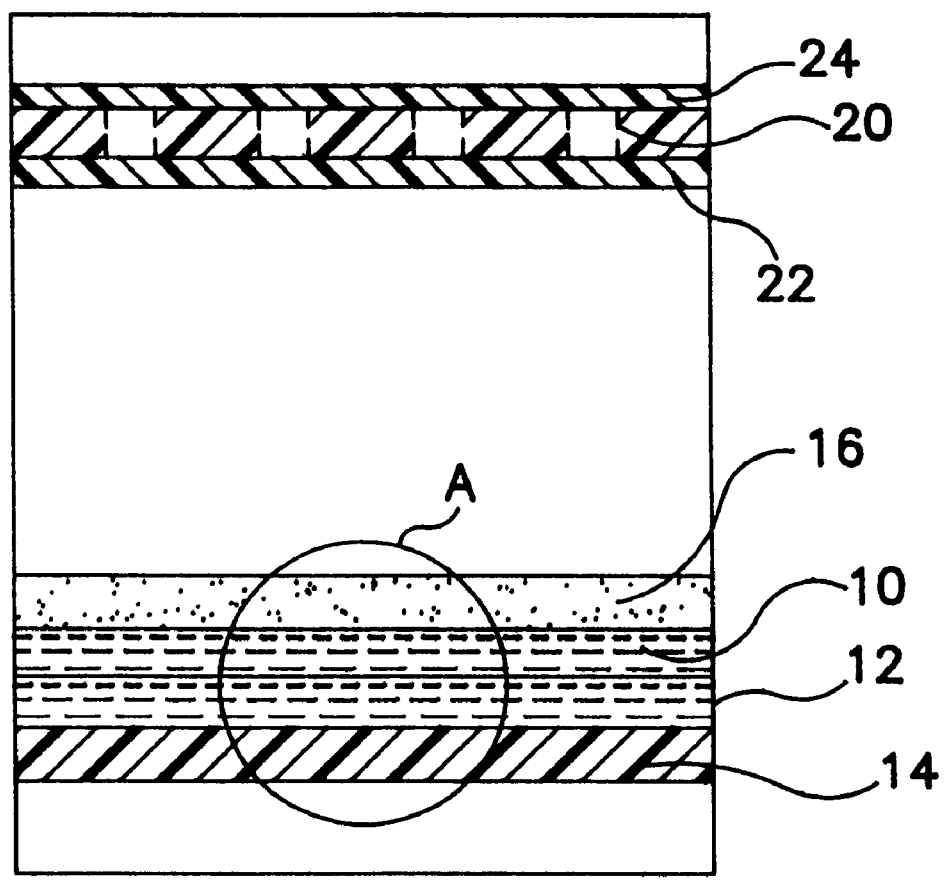
FIG. 10 is a cross section of the sensor plate.

Within the container of the sensor plate device, are one or more layers which help to immobilize/absorb the sample so that colonies of microorganisms can grow localized which increases the ability to detect the colonies of microorganisms. In one embodiment, at least one layer in the device has matrixes that adversely affect visualization of microorganisms. As can be seen in FIG. 10, provided are an immobilizing layer (matrix layer) 10 and a sensor layer 12. These two layers, which will be described more fully hereinafter, can also be combined together into a single layer, though it is preferred that the two layers be provided separately. As also shown in FIG. 10, is the plate bottom 14, which is preferably transparent for viewing/imaging changes in the sensor layer due to microorganism growth.

The sensor layer 12 is provided for the purpose of indicating the location of microbial growth by providing a tightly localized dramatic change in the ultraviolet, visible, and/or infrared spectrum. This localized change is detectable on the bottom surface of the plate, opposite the sensor surface near the microbial growth. The sensor layer comprises a material that undergoes a change in a detectable property (e.g. an indicator) which is embedded on and/or in a matrix (support material) which is preferably opaque. By "opaque", it is meant that the sensor layer sufficiently blocks the viewing or detecting (in any relevant electromagnetic region) of the test sample and/or actual microorganism colonies immobilized in the immobilization layer from the opposite side of the sensor layer (e.g. semi-opaque, substantially opaque, or fully opaque). Though it is possible to have a transparent or relatively transparent sensor layer if the test sample is also substantially transparent (in which case the sensor layer undergoes localized changes from transparent to opaque in the presence of microorganism colonies), it is preferred that the sensor layer not be transparent. Improved results are obtained in detecting microorganisms in test samples that could interfere with detection and enumeration if the sensor layer is opaque. If the test sample itself interferes with visualizing/detecting (e.g. with the eye or with an instrument) the presence or growth of microorganisms directly in the immobilization layer, then it is preferable that at least one of the immobilization layer or the sensor layer (preferably the sensor layer) is capable of blocking detection/visualization of the actual test sample and/or actual microorganisms, and instead detect changes in the sensor layer which correspond to presence/growth of microorganisms in the immobilization layer. The immobilization layer can also be opaque, and in one embodiment of carrying out the invention, the sensor layer, the immobilization layer, and the sample are all opaque.

The sensor comprises a solid composition or membrane, with an indicator medium immobilized on or within it The sensor layer is preferably located flush against the inside surface of the container, or in the sealing means used to seal the container or attached to the sealing means, such that the sensor layer is visible from outside. It is preferably affixed to the container to prevent cells, proteins, other solids or other opaque or colored components from getting between it and the container surface. In certain embodiments the sensor layer is separated from the specimen and its growth medium by a membrane or other solid layer.

One embodiment of this invention comprises a sealing means, such as a lid or cap, which may be transparent or which may have a transparent section. The sensor can be placed in proximity to the transparent lid or section of lid or is made part of the lid. When the lid is used to seal the container, the changes in indicator are read through the transparent sealing means. The sealing means may also be made of a material, such as a polymer, which contains encapsulated indicator micelles. A transparent section in either the container or the sealing means is not needed, as long as the material is permeable to the changes caused by metabolism of the microorganisms, and the changes in the indicator are visible on the surface of the sealing means.

Microorganisms in specimens of body fluids, such as blood, containing as few as 1 organism per total sample volume, can be detected using this invention. Such specimens may require a number of days of incubation before the population of organisms reaches a critical level and where a change in a parameter involved in microorganism metabolism can be measured.

The sensor is useful in that: 1) changes in the sensor layer due to microbial metabolism (e.g., increases or decreases in a gas component due to metabolism) are detected from the solid or semi-solid immobilizing layer rather than in the atmosphere over the specimen, 2) because the sensor is affixed to the interior surface of the plate or the closure or sealing means or attached through the outside of the closure or sealing means, measurements can be made from outside the transparent wall of the plate or the sealing means without having to violate the integrity of the plate, 3) the external measurements can be made by visual inspection or with an instrument that measures by reflectance, fluorescence, etc., or by image capture, 4) opaque/colored or fluorescent components in the specimen do not interfere with the ability to detect changes or the measurement of those changes, and 5) a high concentration of indicator molecules can be maintained within a small volume in the sensor (e.g., within the polymer emulsion or on the membrane), such that a change can be easily observed or detected.

The nutritional components that make up a complex microbial medium influence the metabolic pathways used by microorganisms. Organic adds, bases and various gases are produced in proportions dependent on the nutrients available. These products also vary from species to species of microorganism. The presence of these products in the immobilizing layer can change its pH. The sensor layer used in the invention could contain pH sensitive indicators that give a measurable change in response to a pH change. Or, the presence of gases that affect the pH of the indicator, such as $CO_2$, could be measured. Microbial growth can also be detected by measurement of changes in $O_2$ and/or fluorescence. The sensor layer can be designed to respond to decreases in $O_2$ concentration due to metabolism of microorganisms. And an indicator could be selected that undergoes a change in fluorescence rather than a change in color or other parameter. Carbon dioxide is a common metabolite produced by most organisms and, therefore, is the preferred metabolite for detection of microbial growth. Whatever mechanism is utilized, in a preferred embodiment, the sensor layer will undergo a detectable change in response to the presence growth of most microorganisms.

The indicator can be attached either covalently or non-covalently to a support medium. Alternately, the indicator can be encapsulated within a polymer matrix such as being emulsified within a polymer matrix prior to curing.

The sensor layer is preferably affixed inside a suitable transparent vessel or a transparent sealing means, with an appropriate adhesive, if necessary. They may also comprise an integral part of the sealing means or be affixed to the sealing means or within the vessel as an indicator emulsified within a polymer matrix cured in situ. They can also be placed outside the container, as long as a method is provided that allows the metabolic changes due to the microorganisms, to affect the sensor.

A variety of different fluorescent and visible pH indicators can be used as the active molecular species in pH, $H_2$, $H_2S$, $NH_3$, $O_2$ or $CO_2$ sensors. Generally, the only limitations on the selection of indicators are the requirements that they have acceptable dynamic ranges and wavelength changes that are detectable by infrared, fluorescence, reflectance and/or imaging technologies.

Sensors for detecting pH changes in the culture medium according to the invention preferably exhibit a change in fluorescence intensity or visible color over a pH range of about 5.0 to about 8.0.

Indicators for a $CO_2$ sensor should exhibit a change in infrared intensity, fluorescence intensity or visible color preferably between about pH 13 and about 5, and most preferably between about pH 13 to about 9, in order to detect changes in $CO_2$ concentration.

Only certain pH indicator molecules can be bound covalently or non-covalently to a support medium and retain their pH indicating properties. Indicators belonging to the xanthene, phenolphthalein and phenolsulfonphthalein groups are useful. Examples of these include fluorescein, coumarin, phenolphthalein, thymolphthalein, bromothymol blue, thymol blue, xylenol blue, ortho cresolphthalein and α-naphthol benzein.

The support medium can be a substance such as cellulose or certain silicones, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with microbial growth medium.

The pH indicator sensors directly detect pH changes due to the pH environment of the microbial growth medium. However, these sensors can be made to selectively react to gases (e.g., carbon dioxide, ammonia, hydrogen, hydrogen sulfide, or oxygen) due to microorganism metabolism. A selectively semi-permeable composition or membrane could be provided on the sensor layer, such as silicone, latex, teflon, or various plastics characterized by the capacity to selectively permit the diffusion of a gas while preventing the passage of ions. For sensors comprising indicator encapsulated within a polymer matrix, the polymer forming the matrix can act as the semi-permeable barrier that permits the passage of gases but not ions.

In one embodiment, the $CO_2$ sensor is comprised of a plurality of components. The first component is a visual or fluorescent pH indicator, which is reactive at the pH range between 6 and 10. Examples of indicators meeting these criteria are bromothymol blue, thymol blue, xylenol blue, phenolphthalein, ortho cresolphthalein, coumarin, and fluorescein. A second component, if necessary, is an acid, base or buffer, which maintains an optimal pH environment for detection of $CO_2$ by the selected pH indicator. A third component can be glycerol or an equivalent emulsifier, which can produce droplets of indicator solution emulsified within the uncured polymer. A fourth component can be a pigment, such as titanium oxide, zinc oxide, magnesium oxide, ferrous oxide, etc. A fifth component can be an uncured polymer such as silicone, which maintains a proper environment for the indicator. Any polymer can be used that does not affect too greatly the chemical activity of the indicator, either from its own chemical or physical properties or its requirements for curing, as long as it is permeable to gases but not ions, and does not have these properties altered when subjected to sterilization. Other silicone polymers that are also satisfactory are those that are cured by high temperature, by catalytic activity, or by ultraviolet vulcanization. An emulsion is prepared from the various components and the polymer is cured to form a semipermeable matrix around the droplets of pH indicator, which permits selective diffusion of $CO_2$ and other gases from the immobilization layer, resulting in localized measurable changes in the sensor layer. The sensor layer can be prepared separately, such as in a mold, cured, and then attached to the plate with an appropriate adhesive, such as a silicone adhesive. Alternatively, and preferably, the sensor is formed on the bottom of the container and cured in situ. After curing, the container with the sensor can be sterilized, such as by autoclaving or gamma radiation. Conveniently, the immobilizing and additional optional layers can be introduced into the sensor plate device before sterilization and thus also sterilized by that process.

In a further example, the sensor layer comprises an indicator solution emulsified in a pigmented silicone matrix. The indicator solution is comprised of thymol blue indicator (0.65 g) dissolved into a solution of 0.8 M potassium hydroxide (10.0 ml) and isopropyl alcohol (10.0 ml). The indicator solution (5.0 g) is then mixed with the pigmented silicone components. The pigmented silicone matrix is comprised of Sylgard 184 silicone (components A (50.0 g) and B (5.0 g)) and white pigment (part #61-18000, Ferro Corp., New Jersey) (1.0 g). The sensor material is then poured and spread onto a plate in a thin layer (approximately 0.2 to 0.5 mm).

In another example, the sensor layer comprises an indicator solution mixed with a pigmented silicone matrix. The indicator solution is comprised of ortho-cresolphthalein indicator (2.0 g) dissolved into a solution of isopropyl alcohol (5.0 ml) and 0.9 M potassium hydroxide (5.0 ml). The indicator solution (2.5 g) is then mixed with the pigmented silicone components. The pigmented silicone matrix is comprised of Sylgard 184 silicone (components A (25.0 g) and B (2.5 g)) and white pigment (part #61-18000, Ferro Corp., New Jersey) (0.5 g). The sensor material is then poured and spread onto a plate in a thin layer (approximately 0.2 to 0.5 mm). In a variation of this example, the above ortho-cresolphthalein sensor layer is covered with an overcoat layer comprising the pigmented silicone matrix.

In still another example, the sensor layer is composed of an indicator solution mixed with a pigment solution and a silicone matrix. The indicator solution is comprised of ortho-cresolphthalein indicator (2.0 g) dissolved into a solution of isopropyl alcohol (10.0 ml), and 0.8 M potassium hydroxide (10.0 ml). The pigment solution is comprised of silicone oil (40.0 g), white pigment (part #61-18000, Ferro Corp., New Jersey) (4.0 g). The silicone matrix is comprised of Wacker Elasbosil RT 601 silicone (components A (200.0 g) and B (20.0 g)) and toluene (40.0 g). The indicator solution (20.0 g) is then mixed with the pigment solution (40.0 g) and silicone components. The sensor material is then sprayed onto a plate in a thin layer (approximately 0.1 to 0.3 mm thick).

In addition to indicators responsive to changes in oxygen, carbon dioxide and pH, as mentioned above, indicators could also be utilized that detect changes in ammonia, oxidation-reduction potential, hydrogen, hydrogen-sulfide, or any other substance that undergoes a change due to the presence or growth of microorganisms. Also, a plurality of different indicators could be used in the sensor layer (or in a plurality of sensor layers).

The sensor layer is preferably opaque so as to prevent properties of the sample (e.g. natural fluorescence, opacity, etc.) from affecting or masking the response of the sensor. The sensor layer preferably changes from one opaque state to another opaque state in the presence of microorganisms, with the change being a detectable change by image capture and processing. As one example, the sensor layer could be an emulsified mixture of ortho cresolphthalein indicator in a white pigmented silicone matrix, with an overlay of white pigmented silicone. Or, the sensor layer could be a pigmented silicone matrix emulsified with one or more indicators such as thymol blue indicator, a xylenol blue indicator, or a "universal" indicator. The matrix in the sensor layer could be a suitable latex, polyurethane, nylon membrane (e.g. charged nylon membrane) or cellulose powder. The sensor layer matrix could also be a silicone matrix, such as Sylgard 184, Wacker 601, or Wacker 934. Or, the sensor layer could be made up of two layers, such as an indicator layer and an opaque layer.

The other main layer in the sensor plate device is the immobilizing layer 10. The purpose of the immobilizing layer is to immobilize organisms in the sample either within a matrix or on the surface of a matrix. The sample itself can be a liquid, semi-solid or semi-liquid (e.g. paste or gel) sample. A liquid sample can be mixed with a dry powdered gelling agent to form an organism-immobilizing gel matrix when mixed. The liquid sample is preferably added to a dry powdered gelling agent already provided as a layer in the sensor plate device. However, a liquid sample could also be mixed with a dry powdered gelling agent, and then both immediately added to the sensor plate device before gelling has occurred. Also, a liquid sample could be applied onto an already gelled matrix, or onto a dehydrated or partially dehydrated gel matrix so as to immobilize the microorganisms on the surface of the gel. A gelling agent could also be imbedded in a support matrix to add physical support. Examples include glass or cellulose synthetic polymer fibers either mixed throughout or in the form of woven or non-woven fabrics. Also, in order to immobilize a sample, the immobilization layer need not be a gelling agent, but rather could comprise a non-gel absorbent material, such as sponge materials, celluloses, glass fibers, filter paper, etc.

More than one gelling agent could be utilized in the sensor plate device, either mixed together or as separate layers. For example, a mixture of guar gum and xanthan gum, combined by weight at an approximate ratio of 2:1, could be used. Other gelling agents could be used singly or in combination, including natural and synthetic hydrogel powders. One or more gelling agents could be combined together selected from gums, agars, agaroses, carageenans, bentonite, alginates, collagens, gelatins, fused silicates, water soluble starches, polyacrylates, celluloses, cellulose derivatives, polyethylene glycols, polyethylene oxides, polyvinyl alcohols, dextrans, polyacrylamides, polysaccharides or any other gelling or viscosity enhancing agents.

Dehydrated and/or partially dehydrated gel matrices for surface colony isolation/immobilization could be used, including one or more synthetic or natural hydrophilic polymers. If more than one gelling agent is used, such could be mixed together or provided in a plurality of layers. In one example, an upper layer could be provided to trap microorganisms on the surface, and a lower layer could be provided as a wicking agent to draw the liquid sample through the upper layer (e.g. a thin agar layer over a modified cellulose absorbent, or a porous hydrophilic membrane over an absorbent pad, polymer or hydrogel).

The immobilization layer must not adversely affect the sensor layer. If the sensor layer undergoes a detectable change due to a pH change, then a very acidic gel layer could adversely affect the sensor layer (also some manufacturing processes are acidic and could leave an add residue that could adversely affect the sensor layer). Furthermore, if the immobilization layer is a powdered gel layer, it should be certain that this layer does not turn acidic when mixed with a sample, as this could also cause the sensor layer to change even in the absence of microorganisms.

As can further be seen in FIG. 10, an optional conditioning layer 16 can be provided on (or within or below) the immobilizing layer. Though illustrated separate from the immobilization layer in FIG. 10, the conditioning materials from the conditioning layer are preferably incorporated into the immobilization layer itself. Conditioning components, whether provided within the immobilization layer or in a separate layer, can include one or more of media for microorganism growth, lytic agents, lytic enzymes, antibiotic neutralizers, surfactants or other materials helpful for improving microorganism detection and/or enumeration capabilities. Conditioning components can also be provided both within the immobilization layer and in a separate layer in the same sensor plate device.

Lytic agents for conditioning can be added for lysing blood cells in the test sample, for allowing for a smoother gel, and/or for better rehydration of the gel. Examples of possible lytic agents include saponin, digitonin, Tweens™, polysorbitan monolaurate, and other surfactants. Lytic enzymes, typically tough not necessarily proteolytic enzymes, may be added for digesting cellular material in a blood sample, for making a smoother gel, and/or for better rehydration of the gel. The lytic enzymes for conditioning can include one or more proteases, for example an enzyme mixture derived from *Aspergillus oryzae*, or the like.

Antibiotic neutralizers may be added for conditioning, in particular for faster and/or better recovery of microorganisms in the test sample. One or more of such neutralizers could be selected from resins, gums, and carbon-based materials (e.g. activated charcoal or Ecosorb™), or one of a variety of enzymes to specifically degrade various antibiotics (e.g. beta lactamase).

Media can also be added for conditioning (whether directly to the immobilization layer or separately). Media is added to provide nutrients for the growth of microorganisms. Though many types of media for different types of microorganisms could be used, if the microorganism is an aerobic organism, the media could include, as one example (an exemplary amount of each being listed in parentheses in g/l): tryptone (17), soytone (3), protease peptone (5), malt extract (2.5), dextrose (2.5) and MOPS (23). If the microorganism is an anaerobic organism, the media could further include the media listed above for aerobic organisms, as well as Hemin (0.005), L-cystine (0.2), Na-m-bisulfide (0.2) and Menadione (0.0005).

For Coliforms, the media could include, as an example, Lactose (5), bile salts #3 (0.8), $K_2HPO_4$ (7), $KH_2PO_4$ (3), $(NH_4)_2SO_4$ (0.5), $MgSO_4$ (0.1), Na-m-bisulfide (0.4) and SDS (0.1). For yeast, mold and other add tolerant microorganisms, the media could include, as one example, dextrose (10), yeast extract (10), $(NH_4)$ citrate (2) and tartaric acid to a pH of 5.5.

As can be further seen in FIG. 10, a wall of the container can be provided with apertures 20, below which is a hydrophobic gas-permeable film 22, and above which is a gas-impermeable (removable) film 24. Or, the container could be provided with an opening in a wall thereof with the gas-impermeable film and the hydrophobic gas-permeable film adhered together covering the opening. If the organism is anaerobic, the gas-impermeable film would be left in place. However, if the organism is aerobic, the gas-impermeable film would be removed at the time of the addition of a test sample to the sensor plate device. Of course, the hydrophobic gas-permeable film need not be provided at all, though it is beneficial for preventing contaminants from entering the container, and for preventing potentially infectious test material from leaking out of the device.

Figure 11:
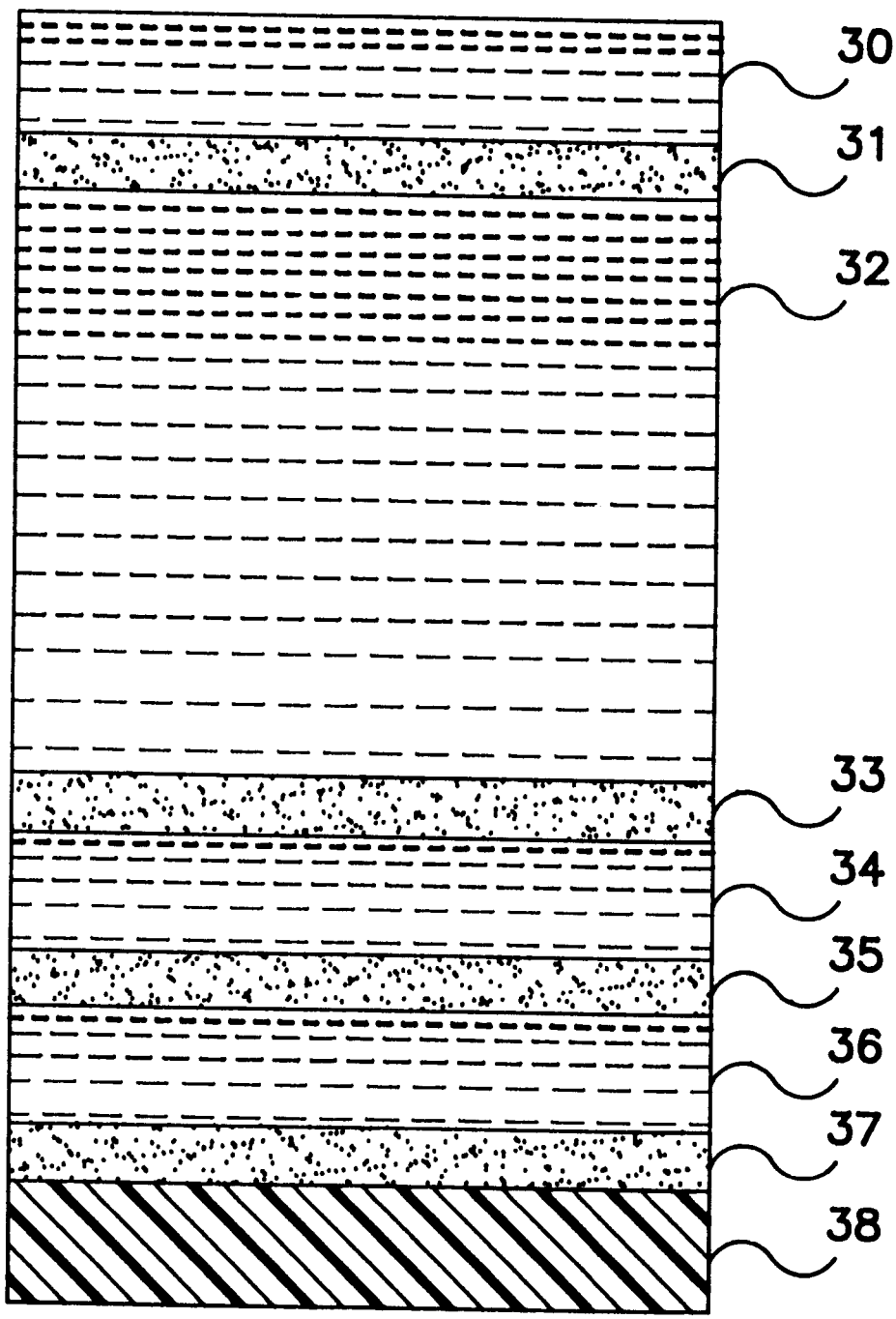
FIG. 11 is a cross section of an alternate embodiment of the sensor plate.
Figure 12:
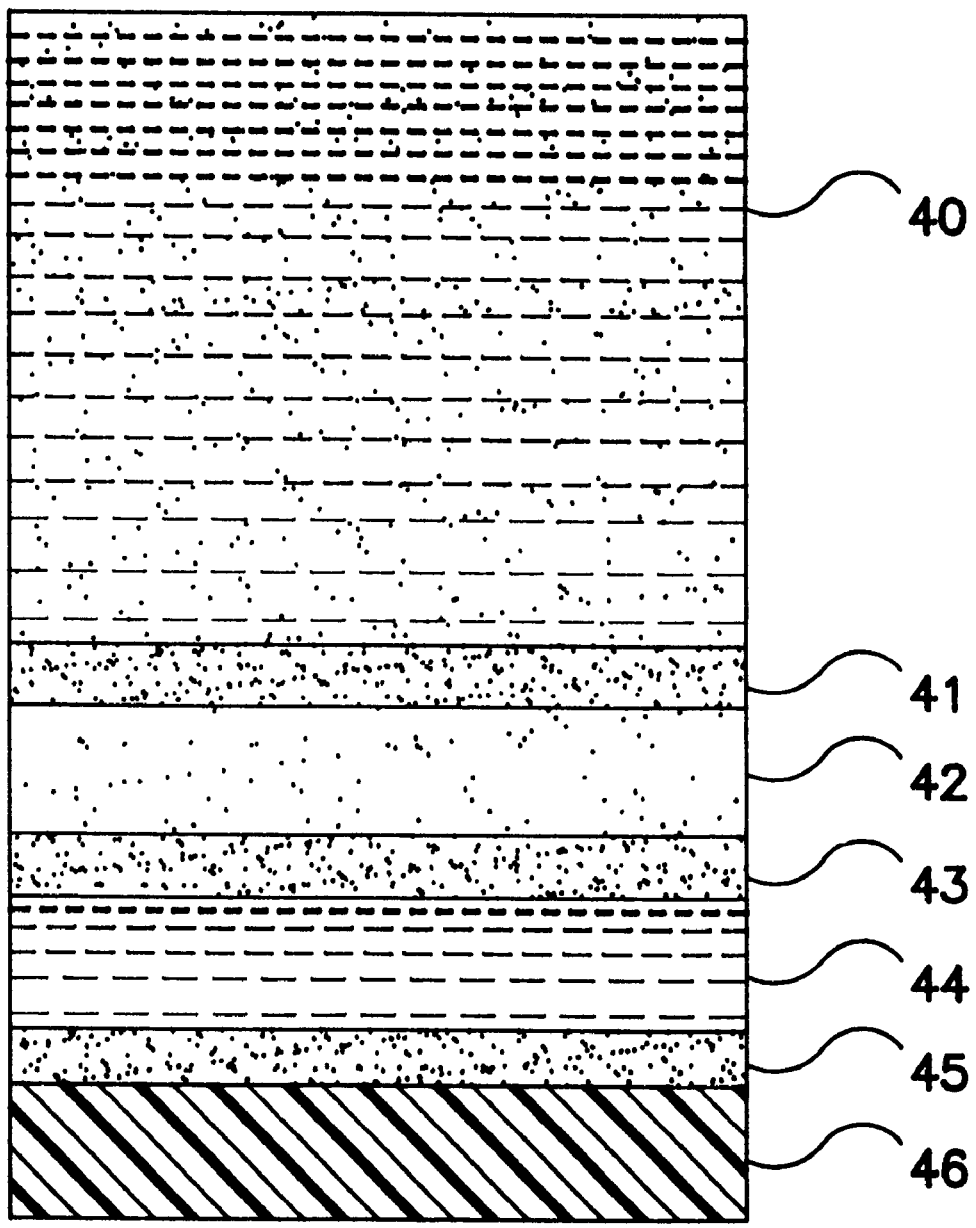
FIG. 12 is a cross section of a further embodiment of the sensor plate.

Area A in FIG. 10 is illustrated in further detail in FIGS. 11 and 12. As can be seen in FIG. 11, in a further embodiment of the sensor plate device, in place of a single immobilization matrix layer, there can be provided one or more of: an isolation gel layer 30 for a semi-rigid surface to allow surface capture and recovery after growth, an adhesive layer 31, an absorptive gel layer 32 and an additional adhesive layer 33. The absorptive gel layer 32 can include one or more of conditioning components (in gels), media for microorganism growth, lytic enzymes, and antibiotic neutralizers. As can be further seen in FIG. 11, in place of a single sensor layer, there can be provided one or more of: an overcoat layer 34, an adhesive layer 35, an indicator layer 36, and an additional adhesive layer 37 in contact with plate bottom 38.

In an additional embodiment of the invention as illustrated in FIG. 12, provided is a matrix layer 40 which comprises: a gelling powder, and dry conditioning components such as media, lytic enzymes and antibiotic neutralizers. As in FIG. 11, in place of a single sensor layer, there can be provided one or more of: an adhesive layer 41, an overcoat layer 42, an adhesive layer 43, an indicator layer 44, and an adhesive layer 45 in contact with plate bottom 46.

The size of the sensor plate device can be varied depending upon the desired sample size. In one example, a sensor plate device has an immobilization layer of the dimensions of 74 mm×117 mm. If the immobilization layer comprises a wet-type gel, then the sample size could be made very small (e.g. 1 ml or less), or, such as with a blood sample, the sample size could be up to 15 ml. On the other hand, if the immobilization layer comprises a dry powdered gel, then the sample size could be even greater, depending upon the amount of the powdered gel (e.g. the sample could be 30 ml or more).

In use, a fluid sample is introduced into the sensor plate device. The sample is "conditioned" (if desired) as it spreads across the bottom surface of the sensor plate. The sample is absorbed into, or forms a gel with, an immobilization matrix layer. The sensor plate is then incubated, promoting the growth of microorganism colonies. A sensor layer located toward a bottom surface of the sensor plate device, undergoes a detectable change so as to indicate the presence of microorganism colonies. Finally, the sensor plate device is inspected manually or automatically to determine the presence and location of microorganism colonies.

The instrument performs three main functions on the sensor plate: plate incubation, image acquisition/capture, and image processing. The instrument provides a controlled environment for incubating plates, which can include a heater if incubation is to take place at an elevated temperature from ambient (though an elevated temperature is not necessary in all situations). A fluid sample is added to the sensor plate device, after which the sensor plate is placed in the instrument where it is subsequently sensed/observed by an image acquisition/capture device (e.g. a camera or scanner) during the incubation period.

Images of the bottom of the sensor plate device can be captured at regular predetermined intervals and subsequently analyzed using one or more image processing techniques and algorithms to determine whether a microorganism colony is present on the sensor plate. The image-processing algorithm implemented to detect and enumerate microorganisms is comprised of one or more of the following steps:

a) Image Masking—to isolate the area of interest from extraneous image data;

b) Image Subtraction—to isolate the areas of change between two images taken at different time intervals;

c) Image Equalization—to amplify the magnitude of the changes appearing in the subtracted image;

d) Image Blurring—to reduce the effects of single pixel noise in the equalized image (low pass filter);

e) Image Contrast and Brightness Enhancement—to further amplify localized differences in the filtered image;

f) Image Thresholding (with several thresholds, if required)—to prepare the image for the colony detection/enumeration algorithm; and/or g) Colony Detection, Enumeration, and Classification—to determine the presence of microbial organisms on the plate, to enumerate the number of colonies on the plate, and/or perform color analysis to classify colonies on the plate.

Figure 13:
FIG. 13 shows the bottom of three sensor plates positive for E. coli.
Figure 14:
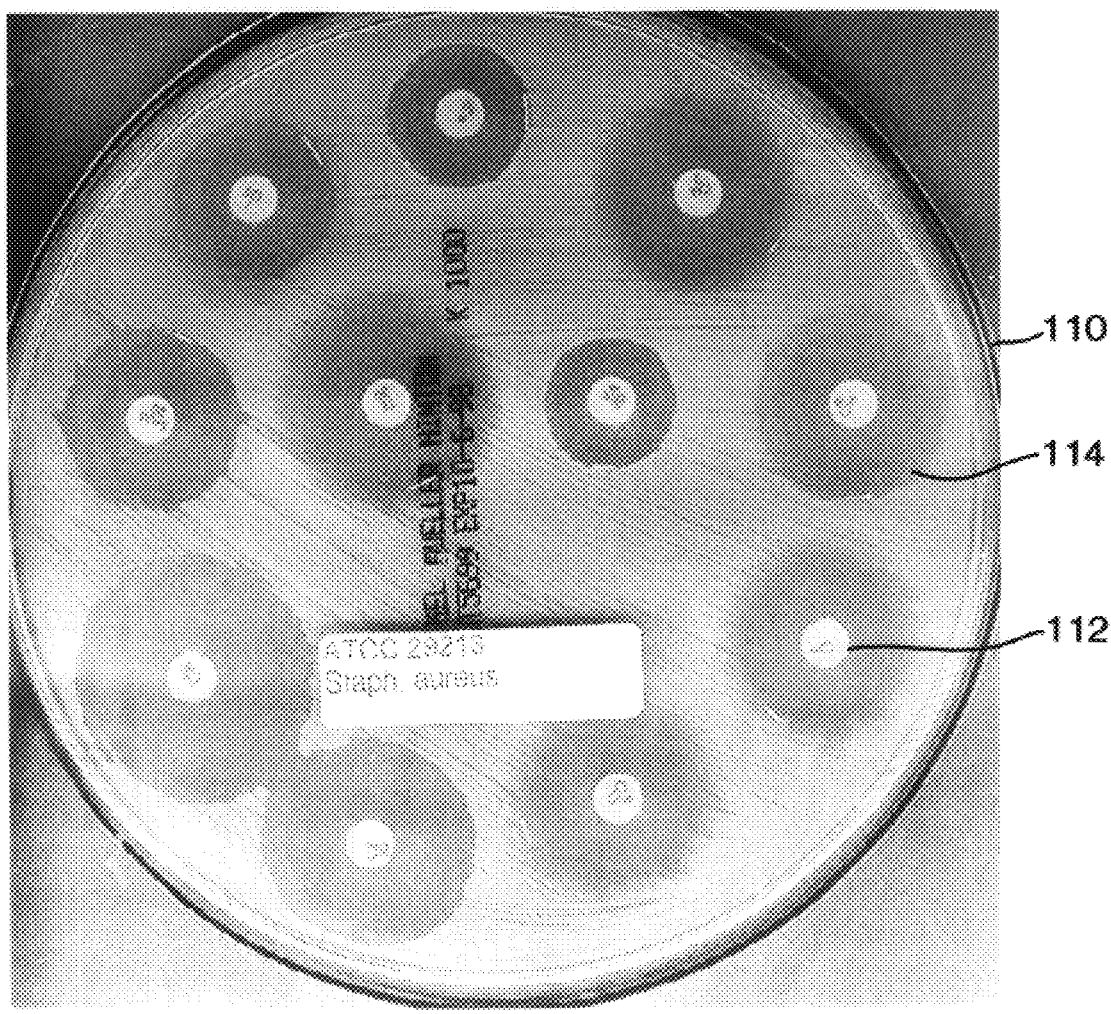
FIG. 14 is an illustration of an agar plate for performing a disk diffusion antibiotic susceptibility test.
Figure 15:
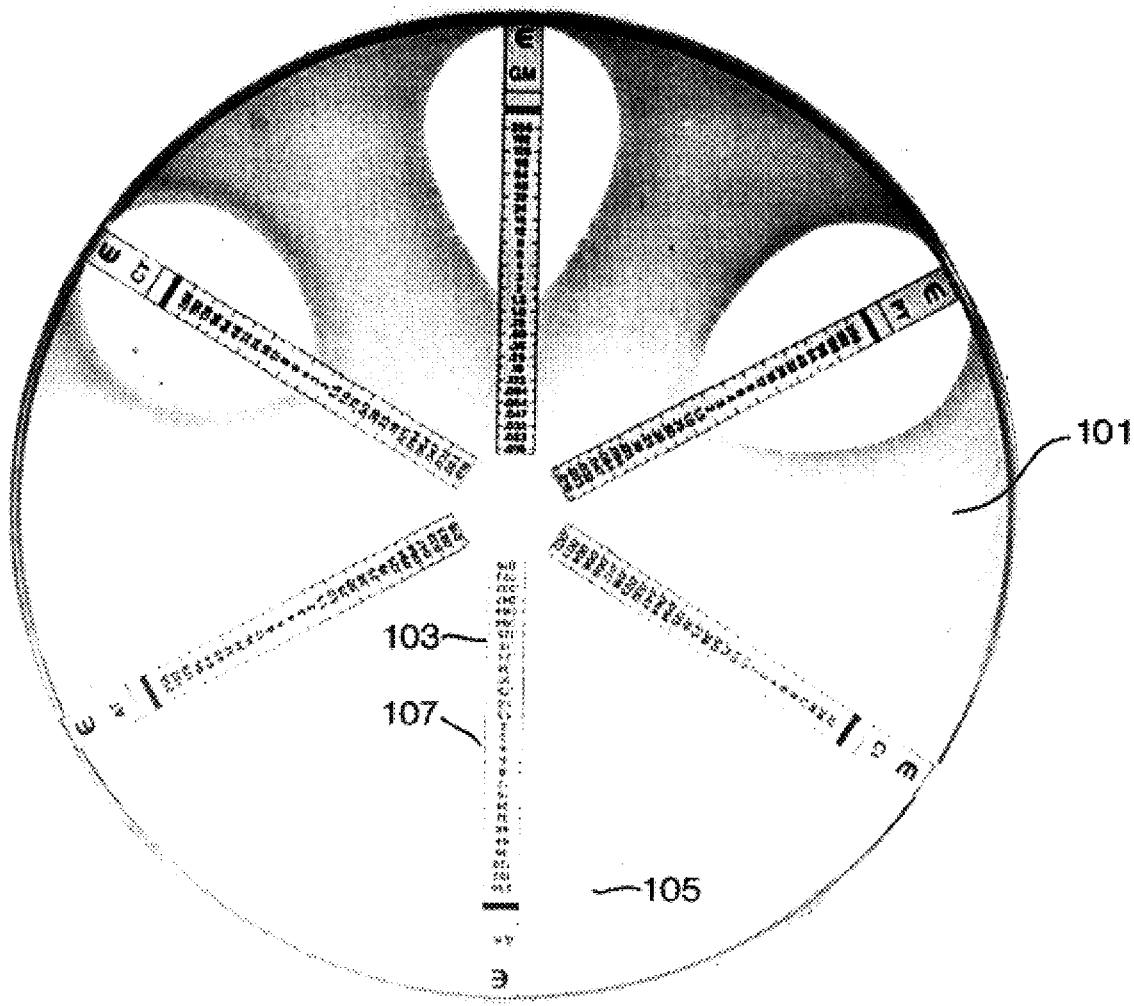
FIG. 15 is an illustration of an antibiotic gradient method for determining susceptibility of a microorganism to particular antimicrobial agents.
Figure 16:
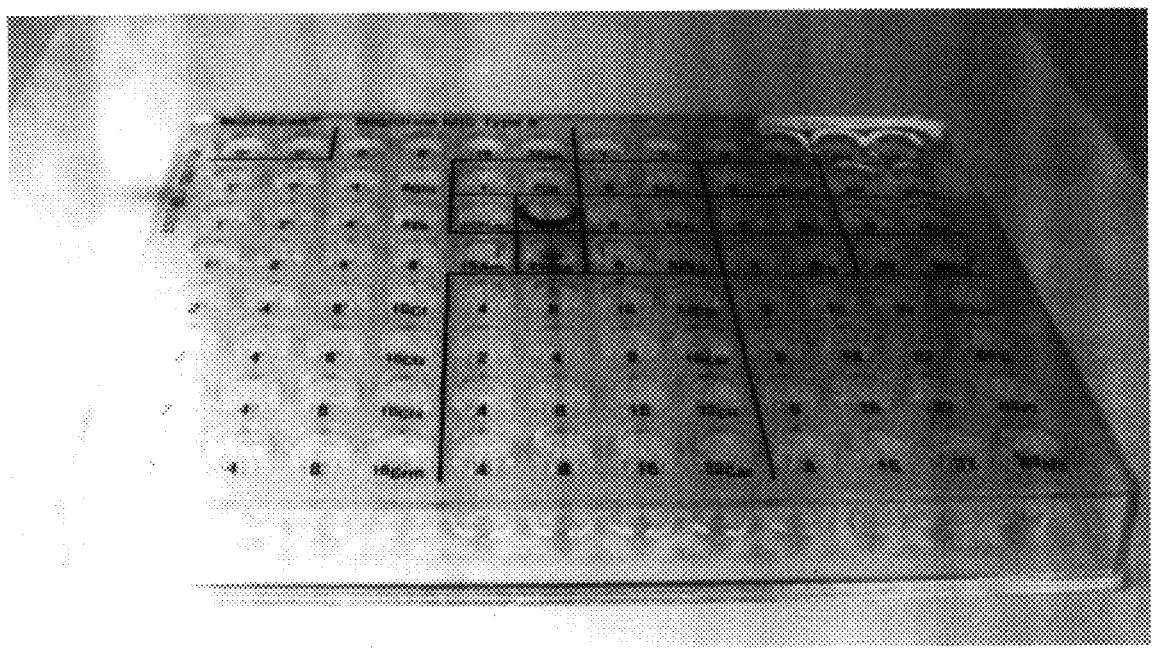
FIG. 16 is an illustration of a device for performing a broth microdilution antibiotic susceptibility test.

Feasibility studies of a number of different types of sensor plate devices have shown good detection results: *E. coli* detected in approximately 6 hours, *E. facaelis* detected in about 10 hours, and *S. aureus* detected in about 11 hours. FIG. 13 shows the underside of four sensor plates where the sensor layer has undergone a detectable change in those areas of the sensor layer proximate to microorganism colonies in an adjacent immobilization matrix layer. Detected colonies in the studies subsequently yielded microbial dilutions that were immediately usable for further testing.

Susceptibility Plate:

Following detection and/or enumeration of microorganisms in a patient sample, it is often desirable to determine to which antibiotics the microorganism is susceptible. There are now a number of bacterial species which increasingly exhibit resistance to one or more classes of antimicrobial agents, making it that much more important to perform susceptibility testing. Failure of a particular susceptibility test to accurately predict antimicrobial resistance in a patient's isolate could significantly impact patient care if an antibiotic is used to which the microorganism is not susceptible.

As part of the present invention, susceptibility plates are provided for performing microbial antibiotic susceptibility testing. The plates are disposable and multi-chambered and are inoculated with a microorganism (any suitable organism such as bacteria, fungi, protozoa, algae or viruses) and anti-microbial agent(s) are applied such that the microorganism is exposed to a variety of concentrations, or a gradient of each anti-microbial agent. The plates are then placed in the instrument, which monitors and measures the growth (or lack thereof) of the microorganisms. This data is used to determine the susceptibility of the microorganism to the antibiotics. Such a system automates antimicrobial susceptibility testing using solid media and Kirby-Bauer standardized result reporting. Thus, the present invention provides a level of automation for susceptibility testing previously associated only with broth microdilution testing, while retaining the advantages of the manual disk diffusion test.

Figure 17:
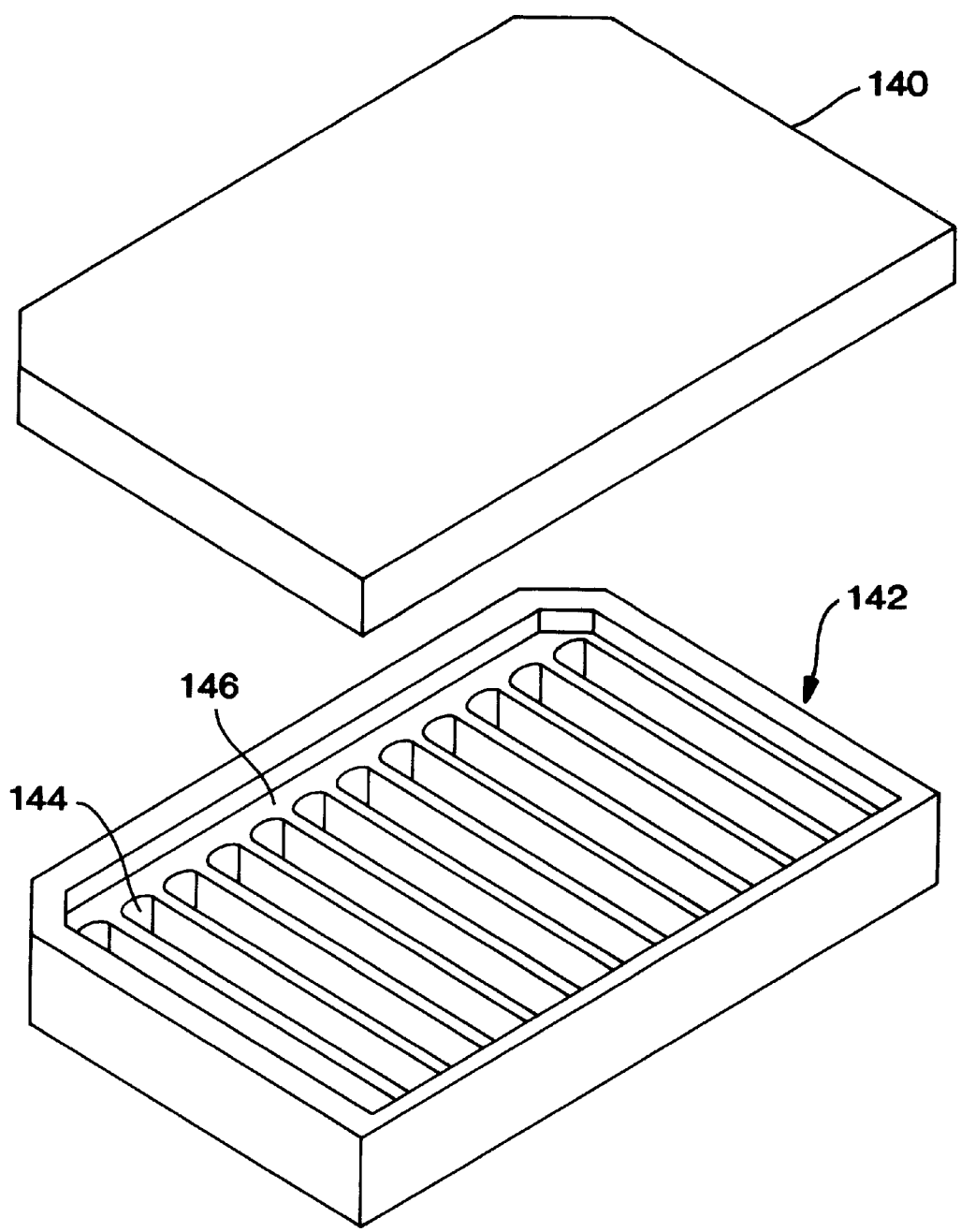
FIG. 17 is an illustration of one embodiment of the present invention having a bottom portion with a bottom gel plate having internal partitions, and a top cover.

One embodiment of the susceptibility plate of the present invention is illustrated in FIG. 17. Such a plate is provided to be disposable and have a low cost for manufacture, and is preferably made of plastic. A top 140 is provided which fits onto bottom 142. Top 140 is preferably transparent or otherwise having properties that can allow viewing (manually or with machine) of microbial growth in the channels in bottom 142. Bottom 142 is provided with a plurality of channels 144 or otherwise mutually isolated chambers. Such channels can be formed within an insert 146 that fits into bottom 142, or bottom 142 and insert 146 can be integrally formed as a single piece (and either or both of the bottom and insert can be opaque). Preferably, marks such as those illustrated along each channel in FIGS. 18 and 19 (or other markings such as numbers) are provided for aiding in manual measurement of the length of inhibition in the channel, if such is desired. This is a definite advantage compared to the standard manual disk diffusion system, where calipers are used to measure a diameter of the inhibition zone, a system that is more labor intensive and less accurate. Each channel 144 contains a growth medium that is solid (or semi-solid). Such growth medium may optionally contain an indicator additive for improving the readability of growth patterns in the various channels. Also, an indicator may be provided in a separate layer (a "sensor layer"), a conditioning layer may be provided, and various components can be provided in the gel layer, such as described in above in relation to the sensor plate.

Figure 18A:
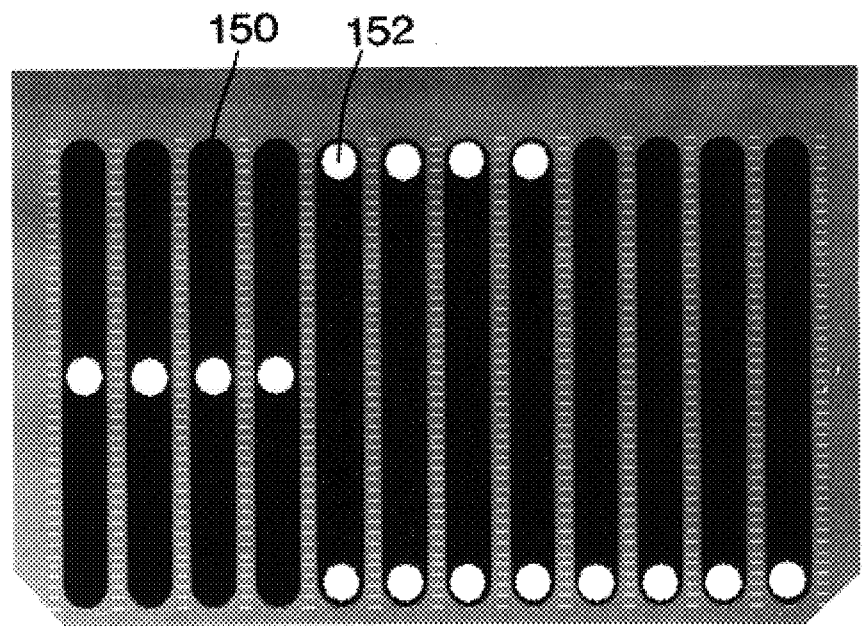
FIGS. 18a and 18b are top views of two embodiments of the invention where
Figure 18B:
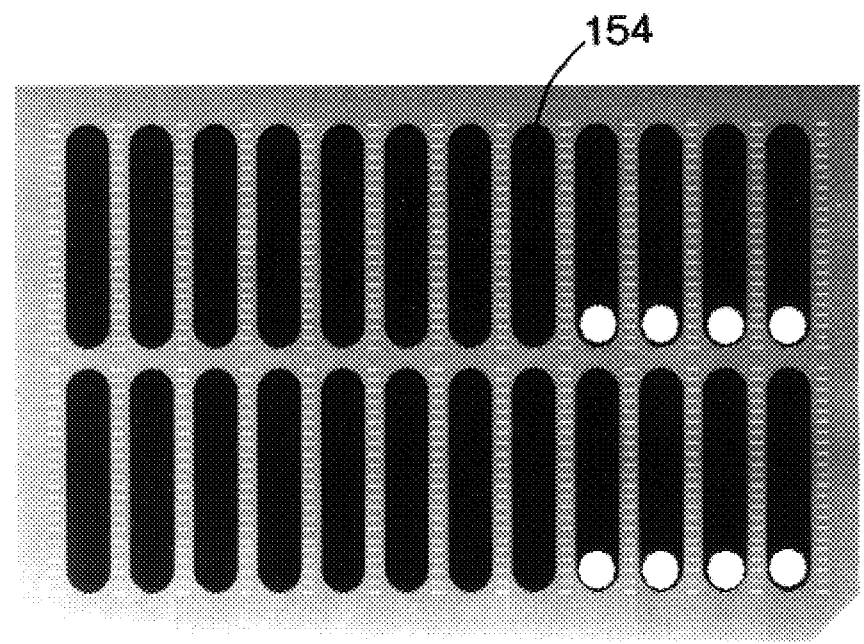
Figure 19A:
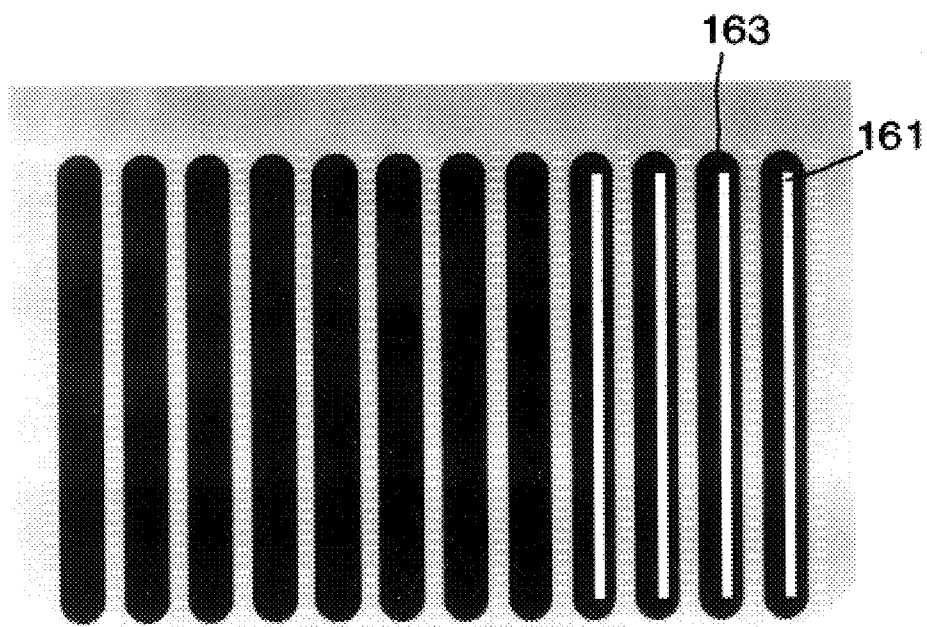
Figure 19B:
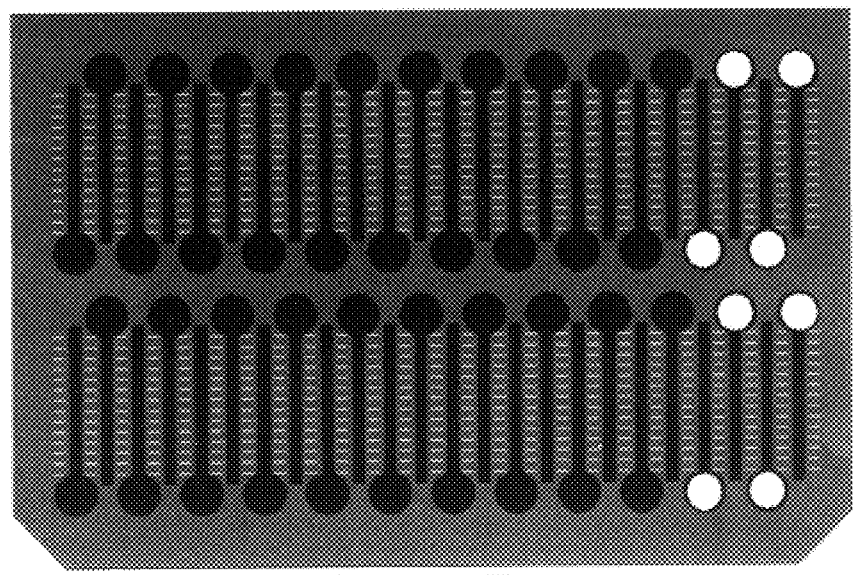
FIG. 19b illustrates an embodiment having thin shorter channels with antibiotic disks at one end thereof.

Physically, the external geometry of the susceptibility plate could be made similar to that of a standard microwell plate (128 mm×86 mm). However, other shapes and sizes are envisioned. The plate could be made to be almost any geometric shape, including square or even round like a standard agar plate. Whatever the external geometry, internally the plate is partitioned into separate chambers or channels in which the solid (or semi-solid) medium is held. The wells or chambers within the plate are preferably elongated channels, though triangular, pie-shaped, circular or square wells, or other geometrically shaped wells, are also envisioned. As an example, FIG. 18a illustrates one embodiment where mutually isolated channels 150 extend almost fully across the width of the plate. Antibiotic disks 152 are placed in each channel at the end or middle of the channel. Shorter channels 154 could also be formed in the plate, such as those illustrated in FIG. 18b. FIG. 19a illustrates a further example where antibiotic gradient strips 161 are disposed in elongated channels 163. In this embodiment, an MIC (minimum inhibitory concentration) can be determined (the MIC is the concentration at the edge of the inhibition zone—the growth/no growth boundary). The separated channels could also be made much narrower, such as illustrated in FIG. 19b. However, if it is desired to use standard antibiotic disks such as those commercially provided for standard Kirby-Bauer antibiotic testing (which disks are approximately 6 mm in diameter), then larger antibiotic disk receiving areas should be provided, such as at the end of each narrow channel. Generally, the channel length is greater than 8 mm (preferably from 20 mm to 45 mm in length), and the channel width is greater than 6 mm (preferably from 8 mm to 16 mm in width). A channel width of approximately 8 mm is most preferred if standard antibiotic disks are used (which are approximately 6 mm in diameter). Of course, if antibiotic disks of different size are used, the channel dimensions could be made larger or smaller. A length of from about 30 to 35 mm is most preferred as this allows sufficient length to detect and measure inhibition zones resulting from nearly all antibiotic/microorganism combinations used in susceptibility testing. The depth of the solid or semi-solid growth medium in the channels should be more than 1 mm, preferably from about 2 mm to about 20 mm, and more preferably from about 5 mm to about 15 mm.

One of the purposes of the isolated chambers is to increase the ease and reproducibility of susceptibility testing, as well as to maximize the number of tests that can be performed on one susceptibility plate. Whereas standard disk diffusion (Kirby-Bauer) tests are physically restricted to a density of 12 tests or less per 150-mm Mueller-Hinton plate (one test per 14.73-$cm^2$), the present invention easily allows for 24 tests or more on a 128 mm×85 mm plate (at least one test per 4.53-$cm^2$), a density of more than 3 times that of the standard disk diffusion plate. Initially it was thought that the length of inhibition area in a channel in the present invention would not correlate with the radius of inhibition on a standard disk diffusion plate (when using the same microorganism and antibiotic). Instead, it was found that the measured length of inhibition was substantially the same in the present invention as the radius measured in the standard plate. By "substantially the same" it is meant that the measured lengths in the present invention and in a standard Kirby-Bauer test after the same period of time were either exactly the same, or close enough that the ultimate outcome of the test (susceptible, intermediate or resistant as defined by the National Committee for Clinical Laboratory Standards, or NCCLS) correlated over 80% of the time, and were within the control ranges outlined by the NCCLS. In most cases the results correlated over 90% of the time. And, in only in a small percentage (<1.1%) of cases did the results of the present invention indicate susceptible when the standard Kirby-Bauer test (with same microorganism and antibiotic) indicated resistant, or vice-versa (<0.9%).

The susceptibility plates of the present invention are used as follows:

1) Disks containing single concentrations, or strips containing several concentrations, of each antibiotic being tested are placed (manually or automatically) onto the inoculated surface of the growth medium in each chamber of the susceptibility plate. Once the disks or strips are placed on the plate, the antibiotics start to diffuse into the growth medium forming an antibiotic gradient within the growth medium. Antibiotic panels are flexible and can be user-configurable and/or pre-configured.

2) The susceptibility plate is placed in the instrument (manually or automatically) where it is incubated, promoting the growth of microorganisms within the chambers, except where inhibited by antibiotics diffused into the growth medium.

3) The susceptibility plate is inspected manually or automatically to determine the presence and length of inhibition zones in the chambers. Ruler markings or numberings along each channel facilitate manual zone measurements. Automatic zone measurements are performed by the instrument via image capture and image processing.

As mentioned above, the length of the inhibition in the channel of the susceptibility plate can be measured manually, or automatically. If automatically, an instrument is provided which is responsible for performing three main functions: susceptibility plate incubation, image acquisition/capture, and image processing. The instrument provides a controlled environment to incubate the plates. Susceptibility plates are inoculated and placed in the incubator where they are subsequently scanned by an image acquisition device during the incubation period. The instrument provides for image acquisition using one or more color and/or gray scale imaging devices: CCD linear array scanner, a CCD line-scan camera, a CCD 2D array camera (still or motion video), a laser scanning camera, or other device that would provide a sufficiently clear image of the susceptibility plate that can be used alone or after further processing. By "image" it is meant any information, such as optical information, from the susceptibility plate that is ≧a 1×1 pixel. The image acquisition is performed at regular preprogrammed intervals, with the captured image obtained from one or more views and angles of the susceptibility plate.

The image-processing algorithm implemented to determine susceptibility is comprised of one or more of the following steps:

h) Image Masking—to isolate the area of interest from extraneous image data;

i) Antibiotic Disk or Strip Detection—to determine identity and concentration of antibiotic under test;

j) Image Subtraction—to isolate the areas of change between two images taken at different time intervals;

k) Image Equalization—to amplify the magnitude of the changes appearing in the subtracted image;

l) Image Blurring—to reduce the effects of single pixel noise in the equalized image (low pass filter);

m) Image Contrast and Brightness Enhancement—to further amplify localized differences in the filtered image; and/or n) Inhibition Zone Detection, Measurement, and Inspection—to determine the susceptibility of microbial organisms to a particular antibiotic.

Figure 20A:
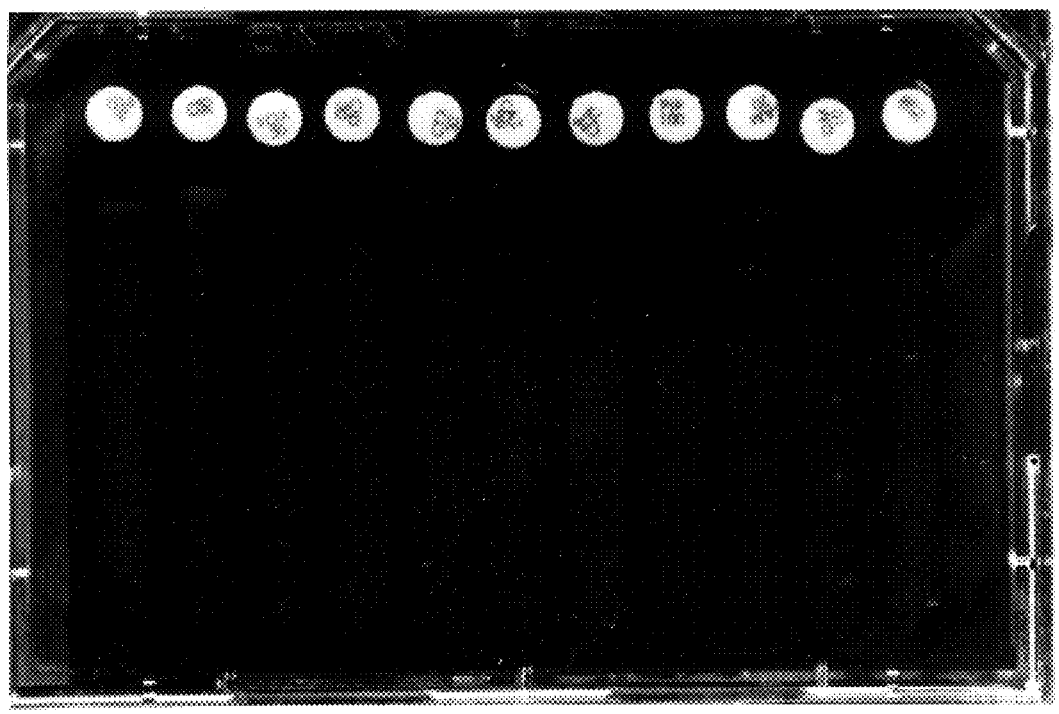
FIGS. 20a and 20b are views of a susceptibility plate with E. coli where
Figure 20B:
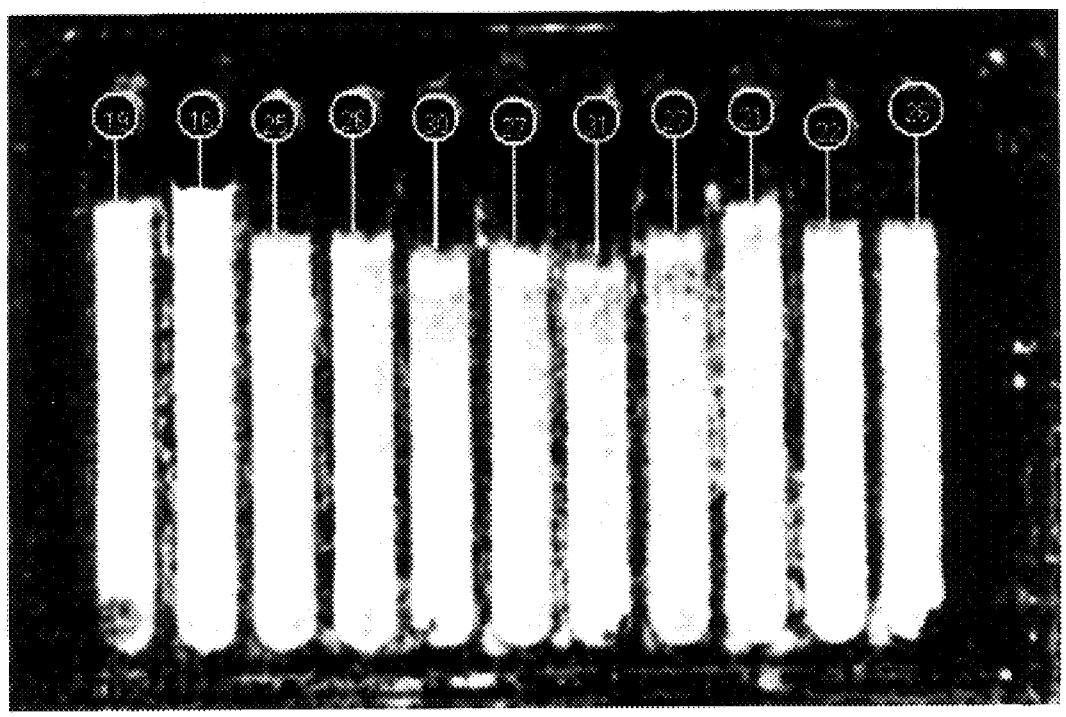
Figure 21A:
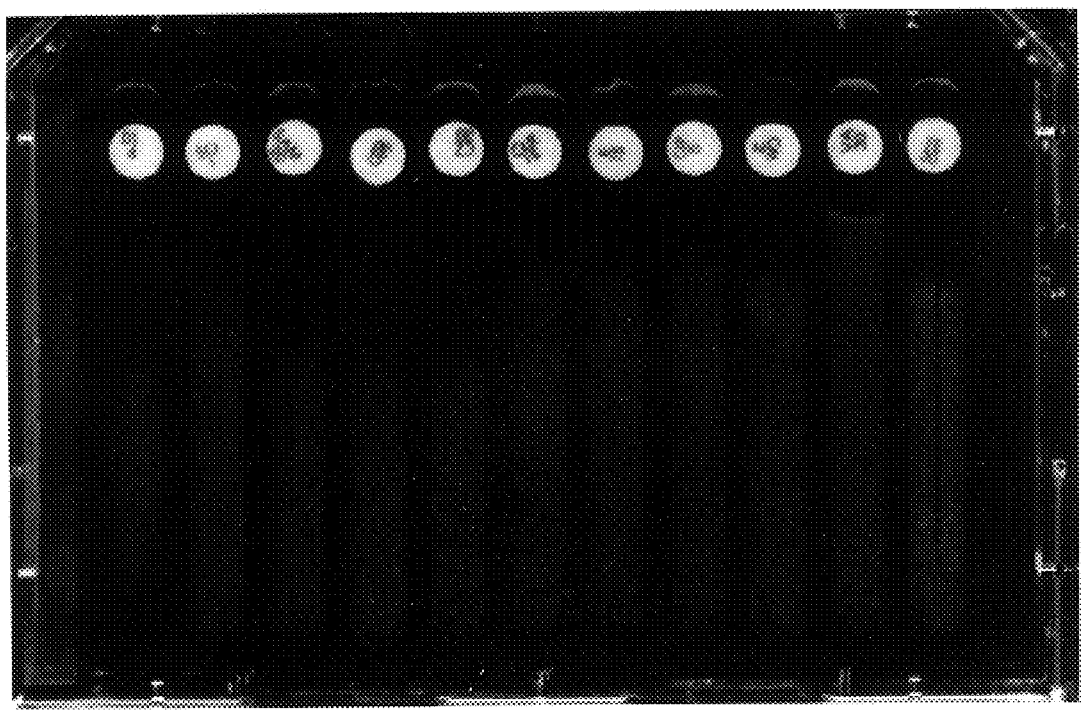
FIGS. 21a and 21b are views of a susceptibility plate with S. aureus, where
Figure 21B:
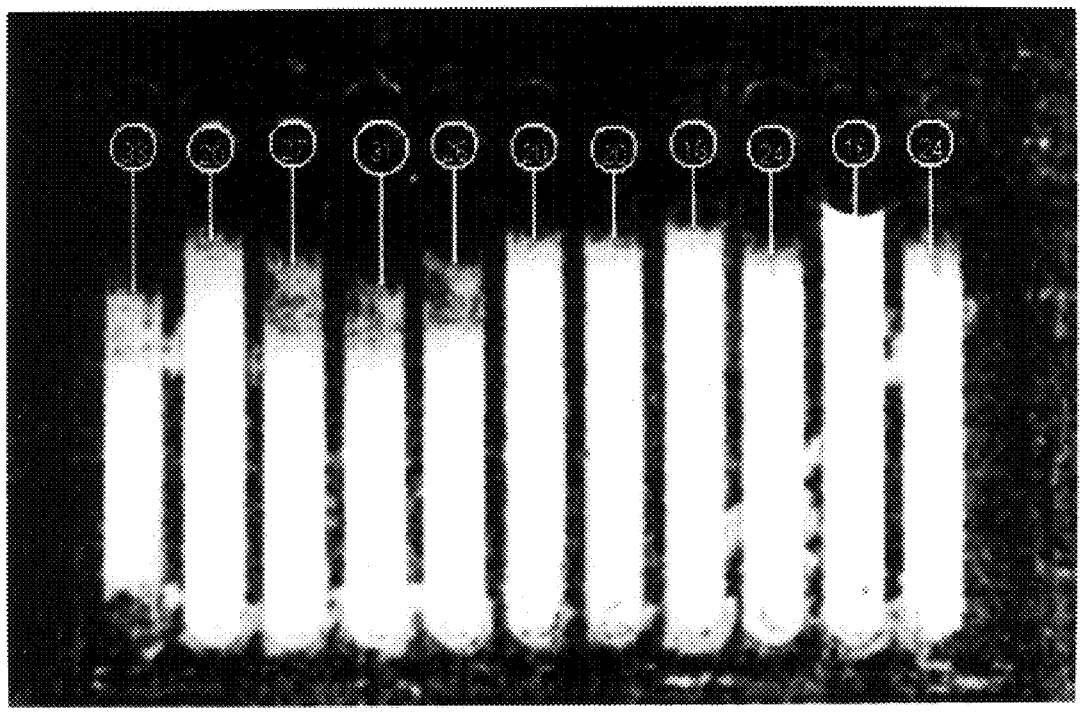

Results of susceptibility testing with system of the present invention are shown in FIGS. 20–22. FIG. 20a shows a grayscale image of *E. coli* on a susceptibility plate (using several different antibiotic disks) taken 18 hours after inoculation and antibiotic disk placement. FIG. 20b is the same plate image after image processing. The image taken at inoculation was subtracted from the image taken after 18 hours of incubation, the difference image was histogram equalized and blurred, and the zone measurement algorithm was applied to the resulting image. Inhibition zones and equivalent diameter measurements are shown in FIG. 20b. Similarly, FIGS. 21a and 21b show a grayscale image and processed image for *S. aureus* using the same timing and processing techniques as for FIG. 20.

Figure 22A:
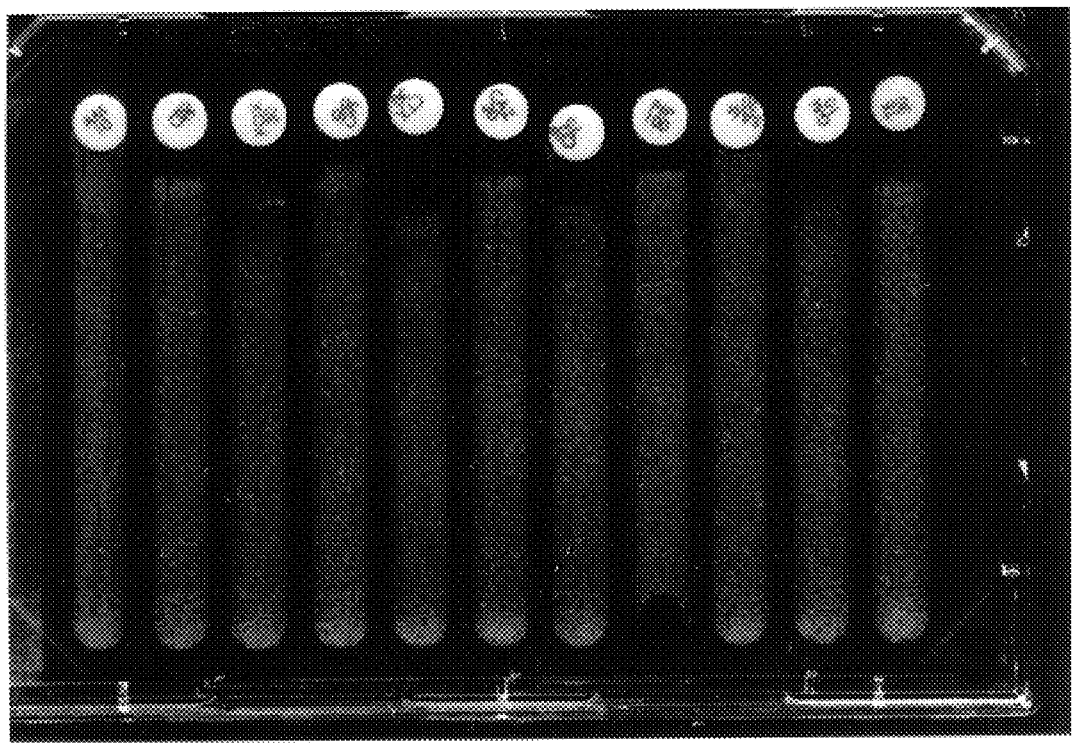
FIGS. 22a to 22d are additional views of a susceptibility plate for Kleb. pneumoniae, where
Figure 22B:
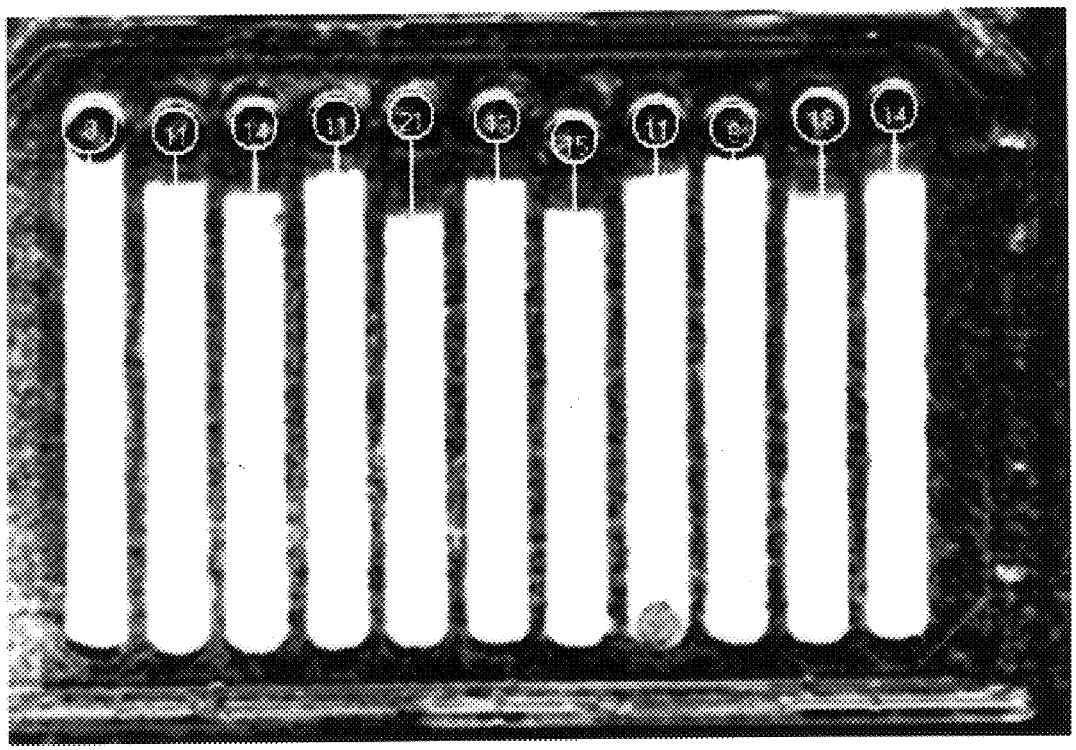
Figure 22C:
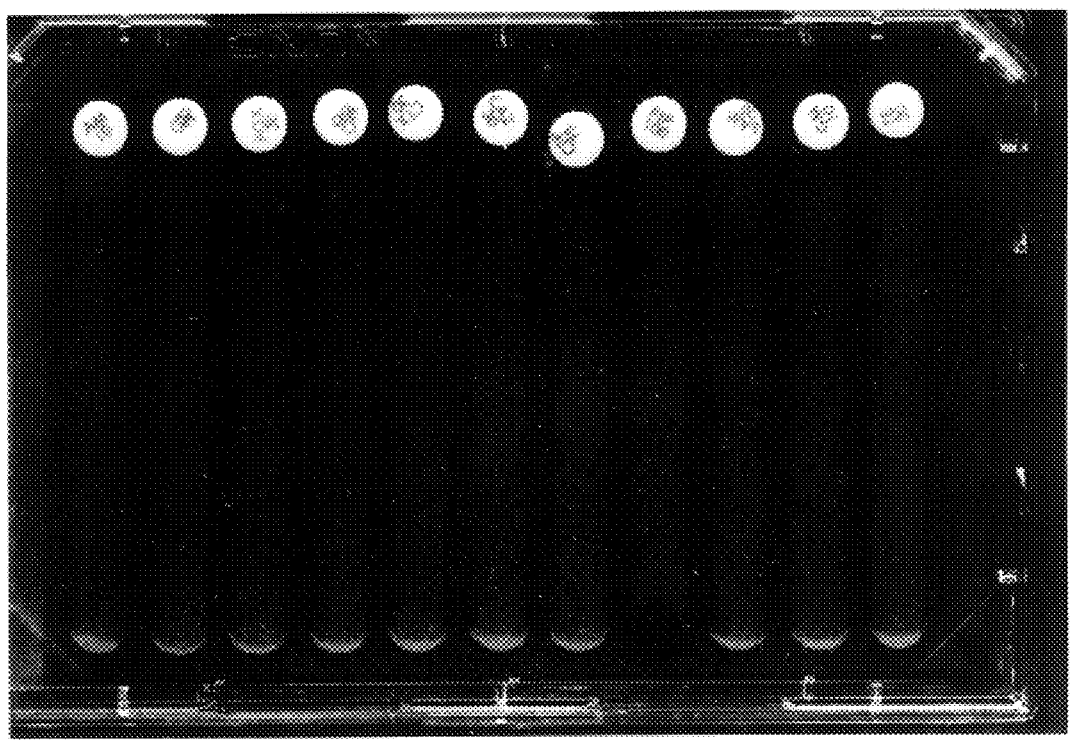
Figure 22D:
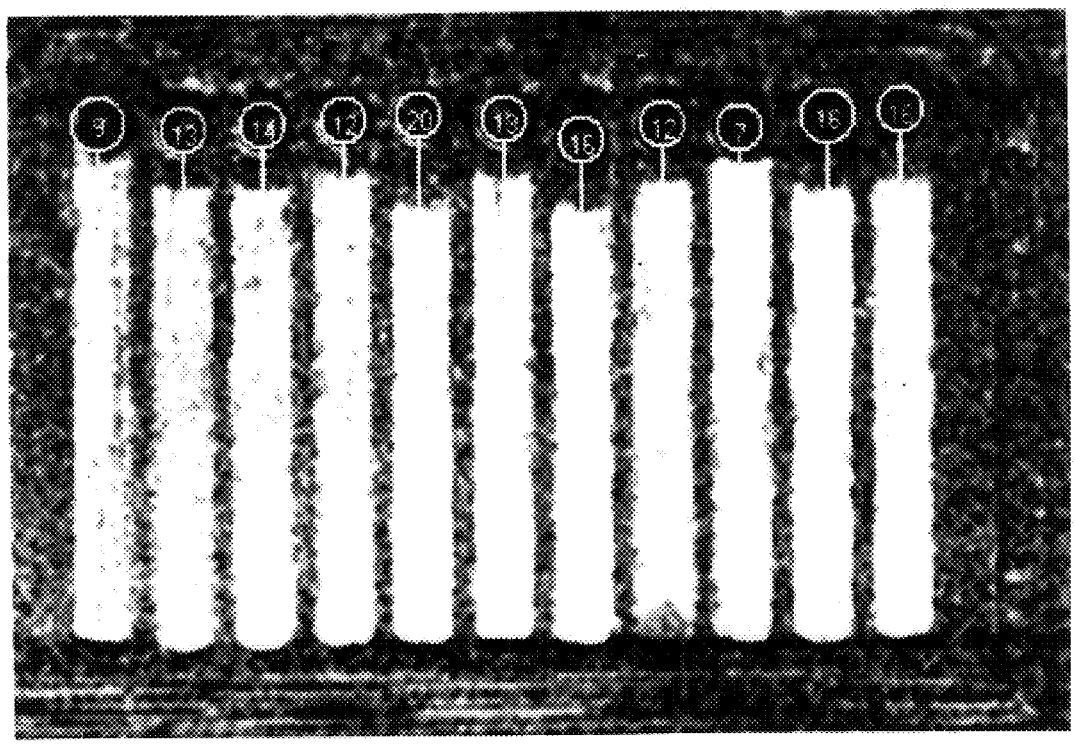

Analyses of images acquired each hour from 1 to 17 hours after inoculation demonstrate the presence of additional information regarding the interaction between the microorganisms and the antibiotics. Properties such as the growth rates of the microorganisms, the diffusion rate of the antibiotics, and the characteristics of the antimicrobial effect on the microorganism are evident. In fact, in a number of instances, the inhibition zones are defined as early as 4 to 6 hours after plate inoculation and using image processing. As an example, FIGS. 22a and 22b show a grayscale image and processed image, respectively, of *Kleb. pneumoniae* only four hours after inoculation (FIGS. 22c and 22d are grayscale and processed images, respectively, of the same plate after 18 hours).

The invention is also envisioned as comprising a top plate and a bottom plate where the bottom plate is a single chamber filled with the solid or semi-solid nutrient medium for the microorganisms and the top plate is provided with a plurality of ribs or dividers. When the top and bottom plates are fitted together (after placement of antibiotic discs within the "chambers" of the top plate) the nutrient medium is separated into isolated chambers as in the embodiment of the invention illustrated in FIG. 4. Of course, the ribs or dividers could be provided as a separate element from the top plate.

Another aspect of the invention is, rather than determining susceptible, intermediate or resistant, the determination of the MIC. In the present invention, MICs can be determined using a regression analysis of the zone measurement (the length of inhibition along the channel), as the diffusion of antibiotic out of the disk forms a highly predictable logarithmic gradient. Determining the MIC from the length of the disk diffusion can be performed by any known method, such as that of BIOMIC™ System by Giles Scientific (N.Y.).

In accordance with the invention, the antimicrobial agent can be applied to a plurality of compartments in differing concentrations. The solid or semi-solid growth medium should be sufficiently solid so that the antimicrobial agent when applied to the growth medium, will diffuse over time and form a concentration gradient (the concentration gradient can be formed in a horizontal direction and can continue to diffuse over a period of up to 10 to 18 hours or more). The solid or semi-solid growth medium in each chamber of the susceptibility plate is inoculated (e.g., swabbed) with a McFarland 0.5 standardized suspension of the microorganism being tested. If the microorganism is a bacterium, it can be an aerobic gram-positive organism, aerobic gram negative organism, anaerobic gram positive organism, anaerobic gram negative organism or a cell wall deficient organism.

The solid or semi-solid growth medium may comprise one or more of routine media, selective media, differential media, selective-differential media, enriched media, susceptibility media, anaerobic media and fungal media. If the media is routine media, it can comprise one or more of trypticase soy blood agar, trypticase soy agar, tryptic soy, BHI blood agar, BHI agar, Casman blood, HBT bi-layer media, and standard methods agar. If the media is selective media, it can comprise one or more of, columbia CNA blood, azide blood agar, chocolate selective, Brucella blood, blood SxT, Strep selective I & II, PEA, Bile Esculin agar, *Clostridium difficile* agar, skirrow, CCFA, CLED, *Pseudomonas cepacia* agar, SxT blood agar, TCBS agar, CIN, *Moraxella catarrhalis* media, and charcoal selective. If the media is differential media, it can comprise one or more of brilliant green, CYE—Legionella, centrimide, DNA-se, hektoen enteric agar, Jordans tartrate, mannitol salt, LIA, TSI, FLO—Pseudomonas F, TECH—Pseudomonas P, Sellers, starch agar, thermonuclease, Tinsdale agar, McCarthy, LSM, sorbitol-McConkey, MUG-McConkey.

If the media is selective and differential media, it can comprise one or more of MacConkey, EMB, Baird Parker, BHI blood with antibiotics, BiGGY—mycologic, CIN, *Clostridium difficile* agar, McBride, Pseudomonas isolation agar, S-S agar, tergitol 7, and XLD agar. If the media is enriched media, it can comprise one or more of chocolate, GC chocolate, BHI chocolate, Borget Gengou, heart infusion agar, McCarthy, Regan-Lowe, Thayer-Martin, transgrow medium, cysteine tellurite blood, cysteine tellurite heart, BHT, heart infusion, Loefflers, and serum tellurite. If the media is anaerobic media, it can comprise one or more of columbia base, PEA, CAN, LKV, BBE, Brucella, BHI blood base, KBE, McClung-Toabe, oxgall, Schaedlers, and Wilkens-Chalgren. And, if the media is a fungal media, it can comprise one or more of BHI base, BiGGY, birdseed, corn meal, cotton seed, DTM, sabourauds dextrose, Fuji medium, inhibition mold, Littman oxgall, mycologic, mycophil, Nickersons, SABHI, and trichophytin.

The antimicrobial agents can be one or more of a beta-lactam antibiotic, a cepheme antibiotic, a glycopeptide antibiotic, an aminoglycoside antibiotic, a macrolide antibiotic, a tetracycline antibiotic, and a quinalone antibiotic. If the antimicrobial agent is a betalactam antibiotic, it can comprise one or more of penicillins, uredopenicillins, synthetics, carbapenems and beta-lactam/inhibitors. If it is a cepheme antibiotic, it can comprise one or more of cephalosporins generations I to IV, and carbacephems. Also, the one or more antimicrobial agents can comprise one or more of sulfa agents and derivatives, chloramphenicol, clindamycin, nitrofurantoins, polymyxins and chemical agents.

Identification Plate:

The identification plates as part of the present invention are used for identifying the microorganism that has been detected in a sample. The identification plate is inoculated with a standardized suspension of a microorganism. The plate is then placed in the instrument. The organism interacts with various substrates or substrate/indicator combinations producing a detectable change in the substrate or indicator. The instrument monitors and measures the changes (or lack thereof) of the substrates and/or indicators. This data is used to identify the microorganism.

Physically, the overall dimensions and composition of the identification plate are envisioned to be similar to that of a conventional 96-well microwell plate: a shallow container that has at least a transparent bottom side. The plate may be flat or have a series of depressions. Specific substrates or substrate/indicator combinations in specific gums or gels, and placed on the flat surface of the plate bottom, or in the series of depressions. These gums are capable of absorbing liquid from the suspension of organisms. Alternately, the substrates or substrate/indicators combinations may be impregnated in an absorbent material such as filter papers discs and affixed to the plate or in the depressions in the gels or gums. In one embodiment the paper discs are affixed with xantham gum. The immobilized substrates or substrate/indicator combinations may be completely recessed below the overall plate surface, be level with all overall plate surface, or be raised from the overall plate surface.

The identification plate is used in the following manner.

1. A standardized suspension of microorganisms is prepared from growth plate.
2. The suspension is added to the identification plate.
3. The suspension is localized into multiple sites each containing a specific substrate or substrate/indicator combination.
4. The identification plate is incubated, promoting the metabolic activity of the organisms within each site.
5. The change in color or fluorescence in the sites indicates metabolic activity on the specific substrates.
6. The identification plate is inspected manually or automatically to determine the pattern of metabolized substrates.

The suspension of microorganisms is applied to one end of the identification plate. The geometry of the plate is such that the suspensions flows or is channeled such that all of the localized sites containing substrates or substrate/indicator combinations absorb a suffident volume of the suspension. The localized sites where substrates or substrate/indicator combinations are allowed to absorb the suspension of microorganisms. Excess liquid is removed either by pouring the excess off the plate or alternately, at the opposite end of the plate from where the suspension was applied, a wicking agent absorbs the excess liquid. In either case, the introduction of sample is a simple one-step operation. A lid is applied to prevent evaporation during incubation.

In another embodiment, a three-piece plate is used. This second piece fits above the identification plate and consists of a channel or series of channels, each containing "funnels" which allow the suspension to flow to localized sites containing substrates or substrate/indicator, combinations. Again, excess liquid may be poured off or absorbed by a wicking agent at the opposite end of the plate from where the suspension is applied. This channel/funnel piece may either be left in place or discarded prior to incubation.

The purpose of sequestering the substrates or substrate/indicator combinations is to provide for a localized reaction free from interference caused by competing substrates. The substrates must be of sufficient concentration and remain in the localized site during the addition of the microorganism suspension. The substrates or substrate/indicator combinations may be of several types. Specific substrates may include o-nitrophenyl-β-D-galactoside and other nitrophenyl derivatives. Alternately, the substrates could include 5-bromo-4-chloro-3-indoyl-β-D-galactoside (X-gal) or other "X" derivatives, fluorescent 4-methyllumbelliferyl derivatives or 7-amino-methylcoumarin derivatives. Substrate/indicator combinations may include substrates such as sugars (glucose, lactose etc.), amino acids (lysine, arginine, etc.), fatty acids (oleic acid, palmitic acid, etc.), low molecular organic acids (citric acid, glucuronic acid, etc.) poly-alcohols (glycerol, sorbitol, etc.) and others. Indicators may include, but are not limited to pH indicators such as bromcresol purple, phenolphthalein, etc. or oxidation/reduction (red-ox) indicators. A positive reaction produces a change in either the ultraviolet, visual or infrared spectrum. For analysis of the identification plate, images are acquired from the top and/or bottom sides of the plate at regular intervals (typically, one hour). Scanning at regular intervals provides kinetic substrate data, which may be used to help characterize the microorganisms. The image processing algorithm implemented to determine identification is comprised of the following steps, some of which may be omitted if such processing is not required:

Image Masking (if necessary)—to isolate the area if interest from extraneous image data Substrate Zone recognition (if necessary)—to determine location of the substrate under test Image Subtraction (if necessary)—to isolate the areas of change between two images taken at different time intervals Image Equalization (if necessary)—to amplify the magnitude of the changes appearing in the subtracted image Image Blurring (if necessary)—to reduce the effect of single pixel noise in the equalized image (low pass filter)

Image Contrast and Brightness Enhancement (if necessary)—to further amplify localized differences in the filtered image Image Pattern Recognition—to determine which substrates have reacted An identification of the organism is then accomplished by comparing the reactions of the test organism suspension to known reactivity with different organisms.

Figure 23A:
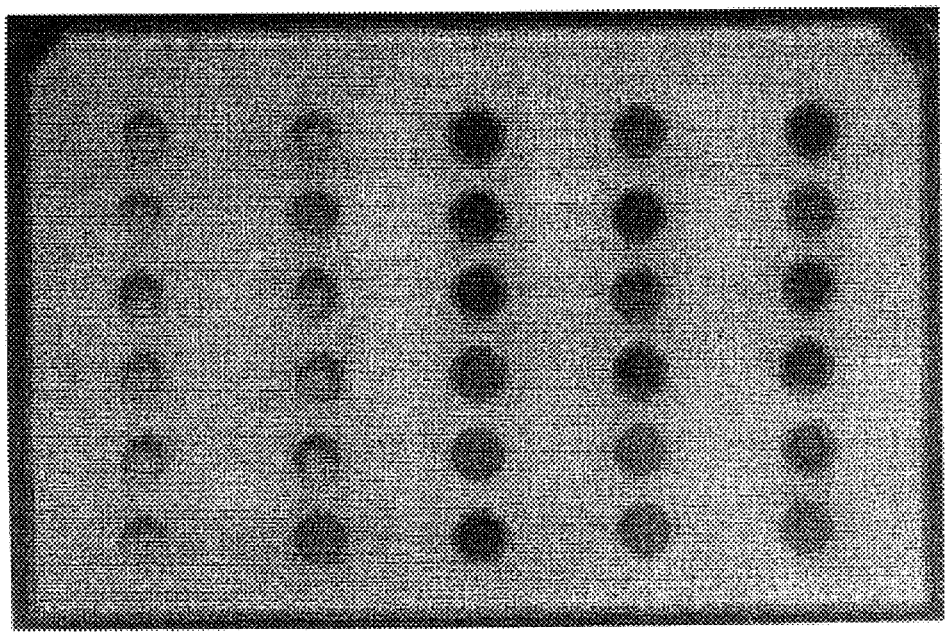
FIGS. 23a and 23b are views of an identification plate, where
Figure 23B:
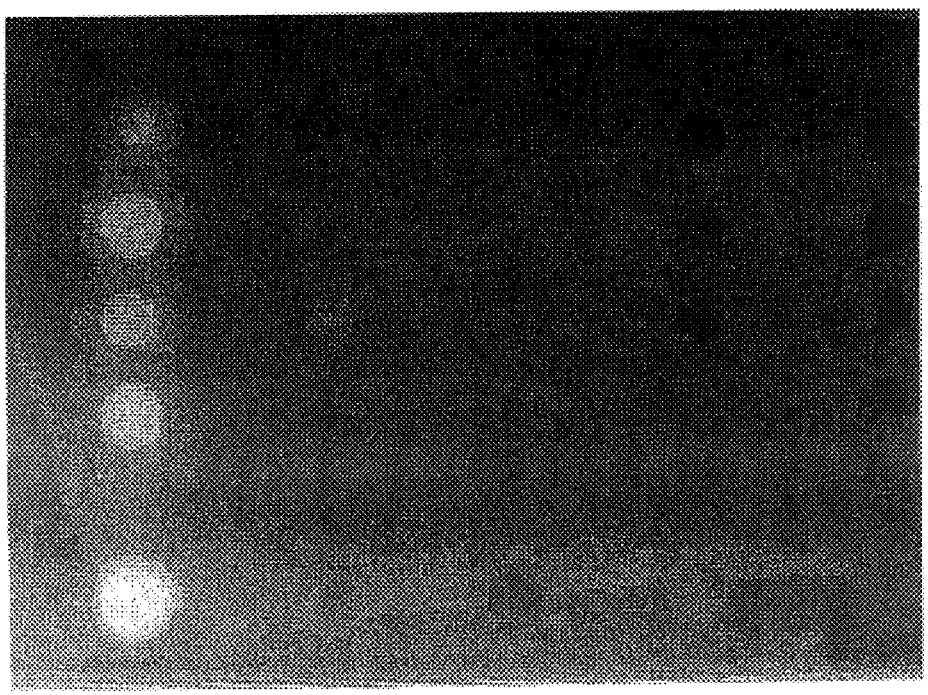
Figure 24:
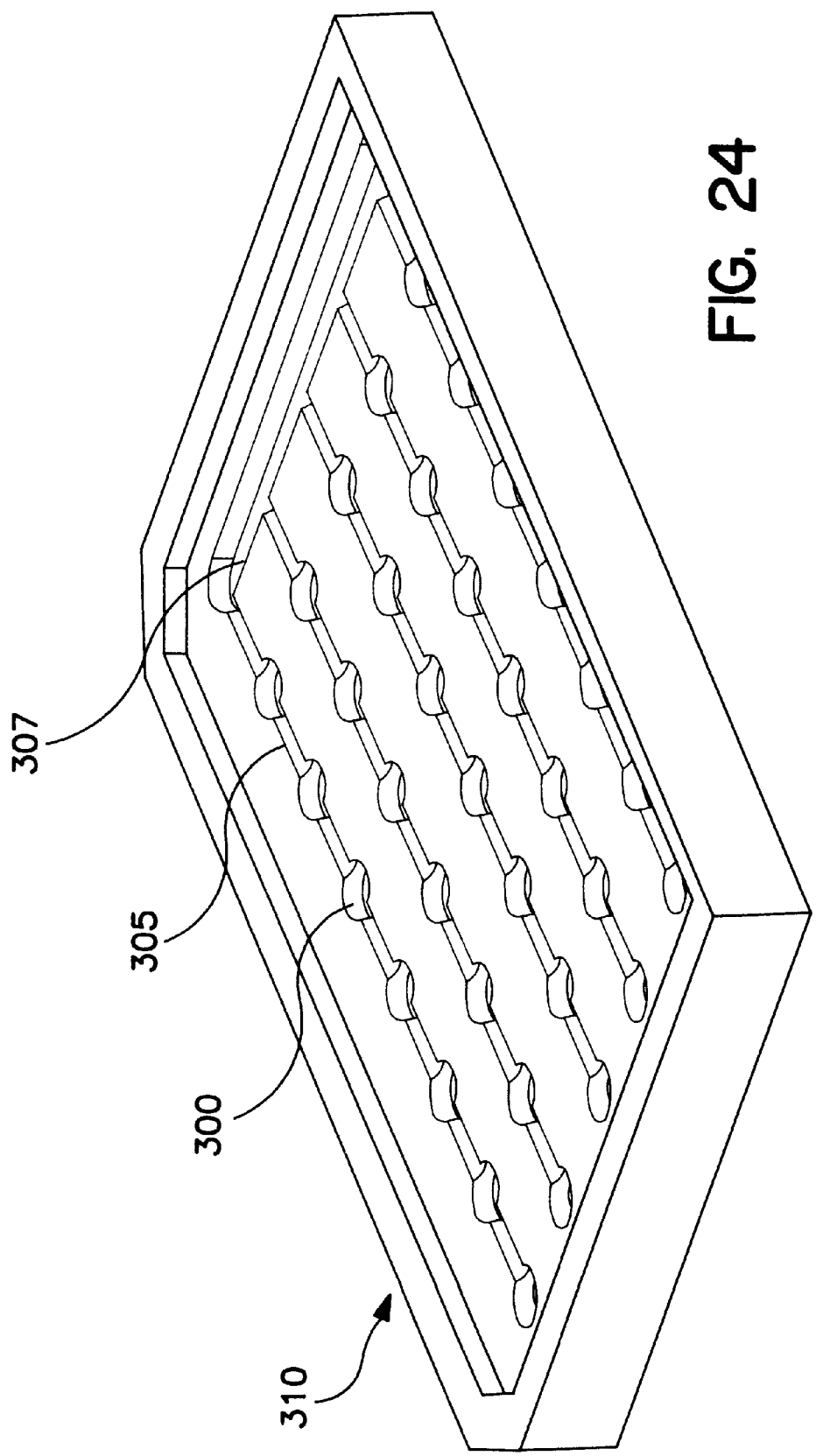
FIG. 24 is another view of the identification plate of the invention.

FIG. 23a is an image (visible) of an identification plate with a plurality of wells at 24 hours, whereas FIG. 23b is an UV image at 24 hours. FIG. 24 is a view of one embodiment of the identification plate 310 where a plurality of wells 300 are provided which may have channels 305 therebetween. A transparent surface can be provided on the bottom of each well, with the remainder of the plate bottom being opaque. A top for the plate can be provided which allows a method of sealing selected wells for anaerobic reactions. The container can be provided with an impermeable top to prevent loss of water vapor, and can be designed to be break-resistant and non-toxic to microorganisms. Barcodes can also be provided on the identification plate (as well as the other types of plates) to indicate information such as what type of plate it is, which patient, etc.

When a sample is added to the plate 310, the liquid is washed over each well 300 via channels 305. Excess liquid can be collected in well 307, in which may be a disposed a sponge or other liquid absorption material. Each substrate/indicator matrix layer is capable of absorbing and retaining 0.05 to 0.1 ml of liquid sample, and prevent cross-contamination of substrates during inoculation. The substrate/indicator is preferably non-toxic to microorganisms and has a shelf life of at least one-year.

Urine Screening Plate:

Although second to respiratory infections in rate of occurrence, urinary tract infections account for the most frequently requested testing in the clinical microbiology laboratory. Clinical urine screening generally includes steps such as streaking an established quantity of urine, typically 1 to 10 microliters, onto plates of both a nonselective medium, typically blood agar, and a selective and/or differential medium such as MacConkey agar, eosin methylene blue (EMB) agar. After incubation, the plates are examined for any microorganism growth, indicating the presence of microorganisms in the sample urine and a possible infection in the patient. Since both the number and type of organisms present in the specimen are clinically relevant, the reading must be done by a trained technician, which can be time consuming and expensive. If required, follow-up testing is done for a more precise identification and antibiotic susceptibility profile.

The instrument of the present invention significantly lightens the load of microbiological testing for bacteriuria. It is capable of detecting and enumerating microorganism colonies on virtually any solid or semisolid medium, whether the medium is opaque, transparent or translucent. The media of choice may include nonselective media such as blood agar and tryptic soy agar, or it could include a selective and/or differential media such as MacConkey agar, EMB agar, cystine-lactose-electrolyte deficient (CLED) agar, as well as media with biochemical substrates added for enhanced differentiation, such as CHROMagar Orientation. Detection and/or enumeration of microbial colonies can be done either by direct imaging of microbial growth, or imaging of direct or indirect changes that the microorganisms make in the media, in indicators, or in a sensor layer. Any combination of media types for culture and detection can be placed in separate compartments or plates for use in the present invention. Preferably, a two chambered plate is used which contains one area of nonselective media and one area of selective and/or differential media. The combination of nonselective and differential media allows a measure of both the total number of microorganisms present and some degree of identification, depending on the specific media selected.

Figures 25A, 25B:
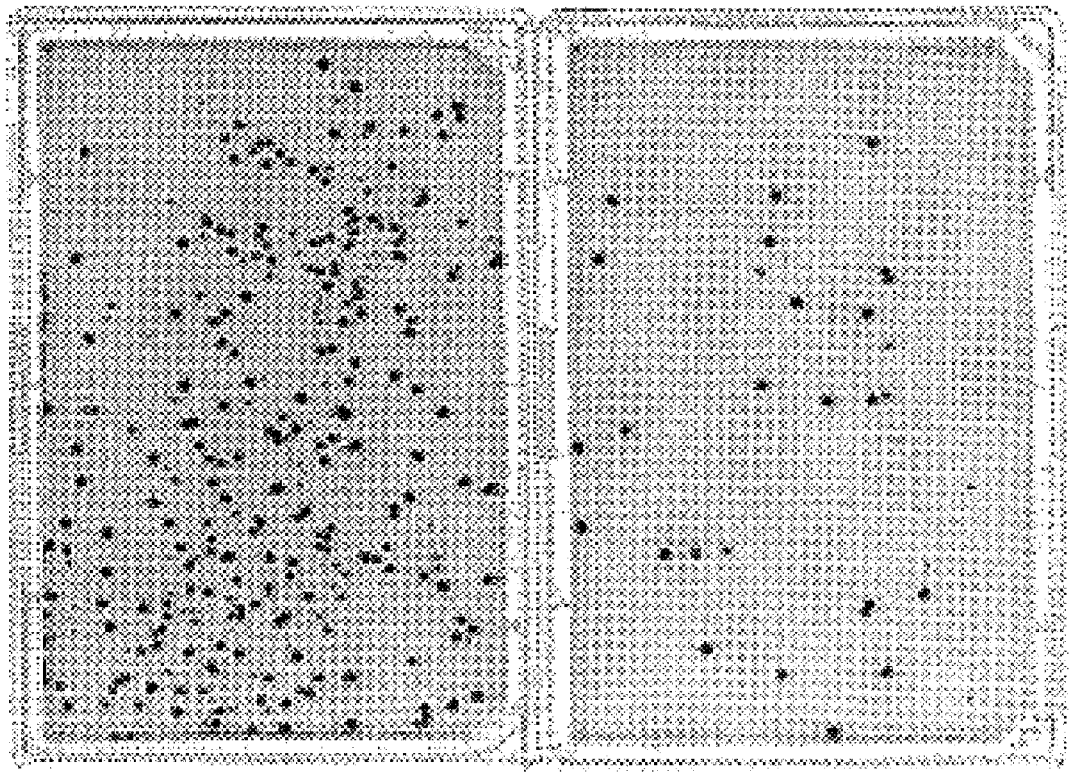
FIGS. 25a and 25b are views of urine screening plates (unprocessed images) taken at 18 hours.

Plates for urine screening are shown in FIGS. 25*a* and 25*b*. For analysis of this type of plate, images are acquired from the top and/or bottom of the plate at regular intervals (e.g. every hour). Or, a single image can be acquired at a predetermined time (e.g. after 24 hours). Though only a single image is necessary to detect and enumerate colonies on a urine screening plate, scanning at regular intervals provides dynamic growth data, which can be used to help characterize the microorganisms. For example, in FIGS. 25*a* and 25*b*, *K. pneumoniae* and *E. fecalis* develop similar color but can easily be distinguished by the fact that *K. pneumoniae* colonies grow at a much greater rate.

The image processing algorithm implemented to detect and enumerate microbial growth on the urine screening plate is comprised of the following steps:

a) Image Masking—to isolate the area of interest from extraneous image data;

b) Image Subtraction (if required)—to isolate the areas of change between two images taken at subsequent time intervals;

c) Image Equalization (if necessary)—to amplify the magnitude of the changes appearing in the subtracted image;

d) Image Blurring (if required)—to reduce the effects of single pixel noise in the equalized image (e.g. a low pass filter);

e) Image Contrast and Brightness Enhancement (if required)—to further amplify localized differences in the filtered image;

f) Color Separation and Analysis (pre-detection or post-detection processing)—to differentiate the types of microbial colonies (indicator-dependent);

g) Image Thresholding (if required)—to prepare the image for the colony detection/enumeration algorithm; and h) Colony Detection and Enumeration—to determine the presence of microbial organisms on the plate, and to enumerate the colonies on the plate.

Studies of the urine screening plates have shown that the colonies can be detected and enumerated at around 12 to 20 hours after inoculation. FIGS. 25*a* and 25*b* are raw scanned images taken at 18 hours. The microorganisms plated were *E. faecalis* (small, light green—when viewed in color), *E. coli* (red), *S. aureus* (small, yellow), *P. aeruginosa* (medium, yellow), *Enterobacter cloacae* (large, dark green), and *Klebsiella pneumoniae* (medium, medium green).

As can be seen by the above description of the present invention, a fully-integrated microbial system is provided—essentially one system that performs nearly all of the functions required by a clinical microbiology laboratory (microbial detection/screening and/or enumeration, microbial identification, antibiotic susceptibility testing, and urine screening). No other fully integrated system is known to exist. Instead, present systems are actually part of a "family" of non-integrated instruments/products where multiple instruments must be purchased (and laboratory space must be found for each) to accomplish the multiple functions of the present invention. The present invention is easier to use and maintain than several separate instruments, it is less expensive to own and operate a single instrument, the present invention requires less laboratory space than several separate instruments, and it is modular and flexible to accommodate a wide capacity range. Not only can the present invention perform multiple functions within the same instrument, but also it can perform these multiple functions at the same time (different types of plates can be disposed adjacent each other). This allows the laboratory user a wide degree of flexibility in scheduling needed tests.

The foregoing description is sufficient to enable one skilled in the art to practice the invention. The examples herein should not be construed as limiting the scope of the claims in any way. Indeed, various modifications of the invention in addition to those shown and described herein will become apparent to those skilled in the art from the foregoing description and fall within the scope of the appended claims.

We claim:

1. A method for performing a plurality of microbiological tests in any order or at the same time, and within the same instrument, comprising:
   a) performing microbiological detection and/or enumeration testing, wherein one or more test samples are added to respective detection plates, each of said plates is placed on or within a holder of the instrument and incubated in the instrument, and during and/or after incubation, each plate is imaged by an imaging device in the instrument in order to determine whether and/or how many microorganism colonies are present;
   b) performing susceptibility and/or identification testing of microorganisms, wherein if susceptibility testing is performed, one or more samples containing microorganisms are added to respective susceptibility plates before or after one or more antibiotics are added to the plate, each of said plates is placed on or within a holder of the instrument and incubated in the instrument, and each plate is imaged by an imaging device the same as or different as the imaging device of step (a) to determine whether and/or the extent of microorganism growth inhibition, and if identification testing is performed, one or more samples containing microorganisms are added to respective identification plates containing substrates for microorganisms, each of said plates is placed on or within a holder of the instrument and incubated in the instrument, and each plate is imaged by an imaging device the same as or different as the imaging devices in steps (a) and/or (b) to classify and/or identify the microorganism(s) on each plate.

2. The method according to claim 1, wherein said imaging device for imaging said one or more detection plates is the same imaging device for imaging said one or more susceptibility and/or identification plates.

3. The method according to claim 1, wherein each of said detection plates and each of said susceptibility and/or identification plates are of the same dimensions and are constructed so as to be interchangeably held by said holders of said instrument.

4. The method according to claim 1, wherein each plate has on a surface thereof, information for identifying the source of the sample thereon and/or the one or more tests to be run on said sample.

5. The method according to claim 4, wherein said information is in the form of a barcode which can be read either by the imaging device or a barcode reader.

6. The method according to claim 1, further comprising one or more transport mechanisms for moving said plates and said one or more imaging devices relative to each other.

7. The method according to claim 6, wherein the same imaging device or devices and the same transport mechanism or mechanisms are used regardless of the type of plate being imaged or moved.

8. The method according to claim 1, wherein said incubation of said detection plates is performed in the same incubator as for the incubation of the susceptibility and/or identification plates.

9. The method according to claim 6, wherein said plates are moved relative to said imaging devices.

10. The method according to claim 6, wherein said one or more imaging devices are moved relative to said plates.

11. The method according to claim 6, wherein both said plates and said one or more imaging devices are moved relative to each other.

12. The method according to claim 1, further comprising monitoring and controlling the instrument functions via a user interface.

13. The method according to claim 1, wherein said imaging of said plates is performed at regular intervals.

14. The method according to claim 13, wherein the imaging of said plates is performed by one or more color and/or gray scale imaging and illumination devices.

15. The method according to claim 1, wherein the imaging of said plates is performed by a plurality of imaging devices.

16. The method according to claim 1, wherein said plates are moved stepwise to imaging stations where they are imaged by said imaging devices.

17. The method according to claim 1, wherein said imaging is performed by one or more of a CCD linear array scanner, a CCD line-scan camera, a CCD 2D array camera, and a laser scanning camera.

18. The method according to claim 17, wherein said imaging comprises capturing an image of each plate at one or more views or angles of each plate.

19. The method according to claim 1, wherein after an image is captured of a plate, the image is processed by using one or more of the following image processing steps: color separation and selection, image masking, image subtraction, image equalization, image blurring, image contrast and brightness enhancement, and image thresholding.

20. The method according to claim 19, further comprising:
   a) colony detection, enumeration and/or classification, if the plate is a detection or screening plate;
   b) inhibition zone detection and measurement, if the plate, or a part of the plate, is for antibiotic susceptibility; and/or
   c) substrate reaction zone inspection, if the plate, or part of the plate, is for microbial identification.

21. The method according to claim 1, wherein said microbiological detection and/or enumeration testing, said susceptibility testing, and said identification testing are performed sequentially and/or concurrently in the instrument.

22. The method according to claim 1, wherein said susceptibility testing and said identification testing are performed on the same plate for the same microorganism being tested.

23. The method according to claim 1, wherein said microbiological detection and/or enumeration testing is performed on one or more detection plates, each having a sensor layer adjacent a microorganism immobilization layer, wherein said imaging of each detection plate is performed on a side of each detection plate proximate to said sensor layer, said sensor layer undergoing a detectable change if microorganisms are present in said immobilization layer, and the imaging device capable of detecting the change in the sensor layer of the detection plate.

24. The method according to claim 1, wherein said susceptibility testing is performed on a plate having at least a portion thereof devoted to determining the susceptibility of a microorganism thereon, said plate having a plurality of channels with antibiotics in each channel and a test sample added to each channel, wherein said imaging is performed on said plate so as to determine the existence and/or degree of inhibition of microorganism growth in each channel.

25. An instrument for performing a plurality of microbiological tests in any order or at the same time, comprising:
   a) one or more plate holders for holding detection plates, and for holding susceptibility and/or identification plates;
   b) a plurality of detection plates for performing microbiological detection and/or enumeration testing, the detection plates held on one or more of said plate holders;

c) a plurality of plates for performing susceptibility and/or identification testing of microorganisms, said susceptibility and/or identification plates held on one or more of said plate holders;

d) one or more imaging devices provided for imaging plates at one or more time periods;

e) one or more transport mechanisms for moving said one or more plate holders and/or one or more imaging devices relative to each other;

f) a computer processor for controlling instrument functions and for processing images obtained by said imaging devices so as to detect the presence of microorganisms on said detection plates and so as to determine antibiotic susceptibility and/or microbial identification on said plates for antibiotic susceptibility and/or microbial identification.

26. The instrument according to claim 25, wherein said one or more plate holders are elongated trays constructed so as to hold a plurality of plates thereon.

27. The instrument according to claim 25, wherein said plate holders are constructed so as to be capable of holding detection plates and susceptibility and/or identification plates at the same time.

28. The instrument according to claim 27, wherein said plate holders are constructed so as to be capable of holding detection plates interchangeably with antibiotic susceptibility and/or identification plates.

29. The instrument according to claim 28, wherein said plate holders are constructed so as to each hold detection plates, antibiotic susceptibility plates, and identification plates at the same time.

30. The instrument according to claim 25, wherein said detection plates are plates each having therein a solid or semi-solid immobilization layer.

31. The instrument according to claim 30, wherein said detection plates further comprise a sensor layer which is capable of undergoing a detectable change due to the presence of microorganisms in the immobilization layer.

32. The instrument according to claim 31, wherein said sensor layer is opaque.

33. The instrument according to claim 25, wherein said testing for antibiotic susceptibility and said testing for microbial identification are performed on the same or separate plates.

34. The instrument according to claim 33, wherein for antibiotic susceptibility, at least a portion of a plate is comprised of plurality of channels or wells having therein a solid or semi-solid nutrient medium.

35. The instrument according to claim 34, wherein each channel or well further comprises an antimicrobial agent therein.

36. The instrument according to claim 33, wherein for microbial identification testing, at least a portion of a plate is comprised of a plurality of channels or wells having therein different microbial substrates.

37. The instrument according to claim 25, further comprising urine screening plates for performing urine screening.

38. The instrument according to claim 25, wherein said one or more imaging devices are devices capable of collecting information from each plate that is greater than or equal to a 1×1 pixel.

39. The instrument according to claim 38, wherein said one or more imaging devices are comprised of at least one of a CCD linear array scanner, a CCD line-scan camera, a CCD 2D array camera, or a laser scanning camera.

40. The instrument according to claim 38, wherein at least two imaging devices are provided, one disposed for imaging a top side of each plate, and a second for imaging a bottom side of each plate.

41. The instrument according to claim 25, wherein said one or more imaging devices comprise a light source for illuminating each plate.

42. The instrument according to claim 25, further comprising an incubator for maintaining an environment conducive to microbial growth.

43. The instrument according to claim 25, wherein said processor performs one or more of the following image processing steps: color separation and selection, image masking, image subtraction, image equalization, image blurring, image contrast and brightness enhancement, and image thresholding.

44. The instrument according to claim 43, wherein said processor performs:

d) colony detection, enumeration and/or classification, if the plate is a detection or screening plate;

e) inhibition zone detection and measurement, if the plate, or a part of the plate, is for antibiotic susceptibility; and/or f) substrate reaction zone inspection, if the plate, or part of the plate, is for microbial identification.

45. A method for detecting and/or enumerating microorganism colonies, comprising:

a) inoculating one or more detection plates, each detection plate comprising an immobilization layer and a sensor layer which undergoes a detectable change when microorganisms are present in the immobilization layer;

b) placing said one or more microbial detection plates on one or more respective plate holders c) incubating said detection plates for a period of time sufficient to allow for microorganism growth and a corresponding change in the sensor layer of each plate having microorganisms therein;

d) taking an image of the sensor layer of each detection plate with an imaging device; and e) processing each sensor layer image to determine whether and/or how many microorganism colonies are present on each plate.

46. A method for performing antibiotic susceptibility testing comprising:

a) adding a test sample to one or more channels of one or more antibiotic susceptibility plates, each channel comprising a solid or semi-solid nutrient medium therein;

b) placing said one or more susceptibility plates onto one or more plate holders;

c) incubating said one or more susceptibility plates;

d) taking an image of each channel of each susceptibility plate; and e) processing each image so as to determine the existence of or extent of microorganism growth inhibition in each channel of each plate.

47. The method according to claim 1, wherein when said plates are imaged, light is illuminated onto one or more sides of each plate being imaged.

48. The method according to claim 47, wherein said light is broadband and/or narrowband visible, ultraviolet and/or infrared illumination.

49. The instrument according to claim 25, further comprising one or more light sources for illuminating each plate being imaged.

50. The instrument according to claim 49, wherein said one or more light sources are a source of broadband and/or narrowband visible, ultraviolet and/or infrared illumination.

51. The instrument according to claim 50, wherein said one or more imaging devices comprises said one or more light sources.

* * * * *

UNITED STATES PATENT AND TRADEMARK OFFICE
CERTIFICATE OF CORRECTION

PATENT NO. : 6,251,624 B1
DATED : June 26, 2001
INVENTOR(S) : Paul M. Matsumura et al.

Page 1 of 1

It is certified that error appears in the above-identified patent and that said Letters Patent is hereby corrected as shown below:

<u>Title page,</u>
<u>References Cited,</u>
"4,217,411  8/1980  Frock" should read -- 4,217,411  8/1980  LeFrock et al. --
"5,290,701  3/1994  Wilkens" should read -- 5,290,701  3/1994  Wilkins --
"N. Balayev" should read -- N. Belayev et al. --

ABSTRACT,
Delete the paragraph after the title "ABSTRACT" and replace with the following paragraph:
A method for performing a plurality of microbiological tests in any order or at the same time, and within the same instrument, comprising: (a) performing microbiological detection and/or enumeration testing, wherein one or more test samples are added to respective detection plates, each of the plates is placed on or within a holder of the instrument and incubated in the instrument, and during and/or after incubation, each plate is imaged by imaging device in the instrument in order to determine whether and/ or how many microorganism colonies are present; and (b) performing susceptibility and/or identification testing of microorganisms If susceptibility testing is performed, one or more samples containing microorganisms are added to respective susceptibility plates before or after one or more antibiotics are added to the plate. Each of the plates is placed on or within a holder of the instrument and incubated in the instrument, and each plate is imaged by an imaging device the same as or different as the imaging device of step (a) to determine whether and/or the extent of microorganism growth inhibition. If identification testing is performed, one or more samples containing microorganisms are added to respective identification plates containing substrates for microorganisms. Each of the plates is placed on or within a holder of the instrument and incubated in the instrument, and each plate is imaged by an imaging device the same as or different as the imaging devices in steps (a) and/or (b) to classify and/or identify the microorganism(s) on each plate.

Signed and Sealed this

Twenty-fifth Day of December, 2001

*Attest:*

*Attesting Officer*

JAMES E. ROGAN
*Director of the United States Patent and Trademark Office*